United States Patent
Tsukamoto et al.

(10) Patent No.: US 6,573,218 B1
(45) Date of Patent: Jun. 3, 2003

(54) FUSED-BENZENE DERIVATIVES USEFUL AS HERBICIDES

(75) Inventors: Masamitsu Tsukamoto, Mayfield Heights, OH (US); Sandeep Gupta, Concord, OH (US); Shao-Yong Wu, Fremont, CA (US); Bai-Ping Ying, Fishers, IN (US); David A. Pulman, Mentor, OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 09/786,816

(22) PCT Filed: Sep. 3, 1999

(86) PCT No.: PCT/US99/18836

§ 371 (c)(1),
(2), (4) Date: Jul. 5, 2001

(87) PCT Pub. No.: WO00/13508

PCT Pub. Date: Mar. 16, 2000

Related U.S. Application Data

(63) Continuation-in-part of application No. 09/149,296, filed on Sep. 9, 1998, now abandoned.

(51) Int. Cl.$^7$ ............... C07D 231/16; C07D 237/04; C07D 239/10; A01N 43/36
(52) U.S. Cl. ............... 504/221; 504/225; 544/51; 544/52; 544/105
(58) Field of Search ............... 504/221, 225; 544/51, 105, 52

(56) References Cited

U.S. PATENT DOCUMENTS

| | | | |
|---|---|---|---|
| 4,859,229 A | 8/1989 | Wenger et al. | 544/313 |
| 4,881,967 A | 11/1989 | Semple | 71/92 |
| 5,082,841 A | 1/1992 | Brown et al. | 514/235.2 |
| 5,169,431 A | 12/1992 | Enomoto et al. | 71/92 |
| 5,346,881 A | 9/1994 | Theodoridis | 504/243 |
| 5,366,955 A | 11/1994 | Nagano et al. | 504/225 |
| 5,416,065 A | 5/1995 | Brunner et al. | 504/246 |
| 5,441,925 A | 8/1995 | Theodoridis | 504/243 |
| 5,521,147 A | 5/1996 | Theodoridis | 504/243 |
| 5,523,280 A | 6/1996 | Chene et al. | 504/280 |
| 5,661,108 A | 8/1997 | Crawford et al. | 504/243 |
| 5,665,681 A | 9/1997 | Seckinger et al. | 504/243 |
| 5,712,225 A | 1/1998 | Hong et al. | 504/223 |
| 5,753,595 A | 5/1998 | Crawford et al. | 504/243 |
| 5,783,521 A | 7/1998 | Rheinheimer et al. | 504/272 |

FOREIGN PATENT DOCUMENTS

| | | |
|---|---|---|
| EP | 0 271 170 A2 | 6/1988 |
| EP | 0 498 590 A1 | 8/1992 |
| EP | 0 640 600 A | 3/1995 |
| JP | 3-81275 * | 4/1991 |
| JP | 9-301973 | 11/1997 |
| WO | WO 93/14073 | 7/1993 |
| WO | WO 95 05079 A | 2/1995 |
| WO | WO 95/33746 | 12/1995 |
| WO | WO 97/08170 | 3/1997 |
| WO | WO 97/08171 | 3/1997 |
| WO | WO 97/12886 | 4/1997 |
| WO | WO 97/29105 | 8/1997 |
| WO | WO 97/42188 | 11/1997 |
| WO | WO 98/27090 | 6/1998 |
| WO | WO 98/38188 | 9/1998 |
| WO | WO 99/06394 | 2/1999 |
| WO | WO 99/31091 | 6/1999 |

OTHER PUBLICATIONS

Machitani et al., Chemical Abstract 115:159132, 1991.*
Chem. Abstr., vol. 58, No. 1, Jan. 7, 1963 (Columbus, OH USA) p. 16340, col. 2, the abstract No. 16340h, Montgomery, J.A. 'Synthesis of potential anticancer agents.' J. Med. Chem. 1965, 8(6), pp. 737–740.
Chem. Abstr., vol. 58, No. 1, Jan. 7, 1963 (Columbus, OH USA) p. 879, col. 1, the abstract No. 879g, EFROS, A.M. 'Action of benzimidazole derivatives on the growth and development of grain–producing plants.' Dokl. Akad. Nauk SSSR. 1962, 146, 236–237.
Javier Catalan et al, Toward the Photostability Mechanism of Intramolecular Hydrogen Bond Systems. 4.$^1$ 3(5)–(1'–Hydroxy–2'–naphthyl)pyrazoles and 3(5)–(2'–Hydroxyl–1'–naphthyl)pyrazoles; J. Org. Chem. 1995, 60. 3427–3439.
Concepcion Lopez et al, A $^{13}$C NMR Spectroscopy study of the structure of N–H pyrazoles and indazoles; Can J. Chem. vol. 71, No. 5 1993, pp. 678–684.
Tetsuju Kawamoto, et al, Synthesis and Reaction of Novel 5–Deazaflavins with Axial Chirality at Pyrimidine Ring Moiety; Tetrahedron Letters; vol. 33, No. 22, pp. 3169–3172, 1992.

* cited by examiner

Primary Examiner—Deepak R. Rao
(74) Attorney, Agent, or Firm—Sughrue Mion, PLLC

(57) ABSTRACT

A compound of the formula (Ia):

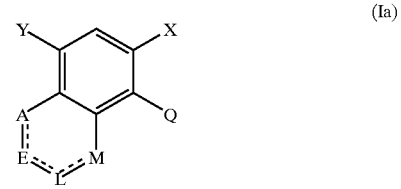

or its salts, in which the variables are as described in the disclosure; herbicidal compositions of said compounds, herbicidal processes using said compounds, defoliant processes using said compounds, and processes for preparing said compounds.

15 Claims, No Drawings

FUSED-BENZENE DERIVATIVES USEFUL AS HERBICIDES

This application is the U.S. National Stage Application under 35 U.S.C. § 371 of PCT/US99/18836, filed in English on Sep. 3, 1999, filed as a continuation-in-part application of U.S. Ser. No. 09/149,296, filed Sep. 9, 1998, now abandoned.

BACKGROUND OF THE UNION

1. Field of the Invention

The present invention relates to novel fused-benzene derivatives, their salts and compositions, intermediates, a process for producing them, and their use as herbicides.

2. Description of the Related Art

U.S. Pat. No. 4,859,229 discloses the herbicidal utility of uracil derivatives, in which the phenyl ring of the described compounds did not have any 2,6-disubsutitutions. Recently WO98/38188 and WO99/31091 disclosed benzoxazole and benzothiazole derivatives which have potent herbicidal activity in preemergence and postemergence applications.

The formula is;
wherein;

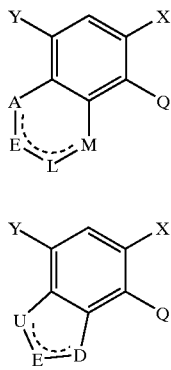

(Ia′)

(Ib′)

Q is uracil and D is either oxygen or sulfur. U.S. Pat. No. 5,169,431 disclosed benzofuran or benzothiophene type derivatives with Q as uracil and D is carbon. WO97/29105 disclosed benzofuran derivatives with Q as uracil and D is oxygen. WO93/14073 disclosed substituted dihydrobenzofuran type compounds with Q as uracil or triazine derivatives and D is carbon. U.S. Pat. No. 5,521,147 disclosed dihydrobenzofuran, dihydrobenzopyran and dihydrobenzofuran-3-one type derivatives with Q as uracil and D or M is oxygen. EP. 0,271,170 disclosed dihydrobenzofuran and dihydrobenzopyran derivatives where Q is many kinds of heterocycles and D or M is carbon. WO95/33746 disclosed cyclic sulfonamide derivatives where Q is many kinds of heterocycles including uracil and D is carbon. U.S. Pat. No. 5,346,881 disclosed benzodioxin or benzodioxole derivatives where Q is uracil, M is oxygen. JP 09301973 disclosed 2H-chromene type derivatives with Q is many kinds of heterocycles including uracil and M is oxygen. WO97/12886 disclosed benzisoxazole or benzisoxazolidinone derivatives where Q is many kinds of heterocycles including uracil and D is oxygen.

WO97/42188 disclosed indole type derivatives with Q as uracil and D or U isnitrogen. Despite the broad coverage of these patents, the general structure of the present invention has not been described.

The specific fused-benzene compounds of the formula (Ia) and (Ib) mentioned below are novel and can be used to effectively control a variety of broad or grassy leaf plant species.

SUMMARY OF THE INVENTION

The invention delineates a method for the control of undesired vegetation in a plantation crop by the application to the locus of the crop an effective amount of a compound described herein. The present application describes certain herbicidal fused benzene derivatives of the formula (Ia) and (Ib) including all geometric, tautomeric and stereo isomers, and their salts, as well as compositions containing them and methods of preparation for these compounds. (Ia) (Ib)

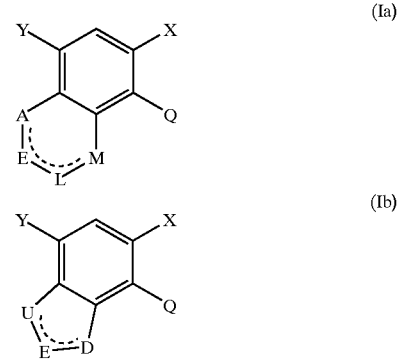

in which

X, Y are independent of each other and are represented by hydrogen, halogen, cyano, nitro, $(C_{1-4})$alkyl, $(C_{1-4})$alkoxy, $(C_{1-4})$haloalkyl or $(C_{1-4})$haloalkoxy;

A is oxygen, nitrogen, $NR_1$, $CR_3$, $CR_3R_4$, $S(O)_n{}^*$, $C(=O)$, $C(=S)$ or $C(=NR_1)$;

D is nitrogen or $NR_2$;

M is $CR_5$, $CR_5R_6$, nitrogen, $NR_2$, $S(O)_n{}^*$, $C(=O)$, $C(=S)$ or $C(=NR_2)$;

When A is oxygen, M is nitrogen, $NR_2$, $S(O)_n{}^*$, $C(=O)$, $C(=S)$ or $C(=NR_2)$;

E and L are independent of each other and may be selected from $CR_7$, $CR_8$, $CR_7R_8$, oxygen, nitrogen, $NR_7$, $S(O)_n{}^*$, $C(=O)$, $C(=S)$, $C(=NR_7)$ or $CNR_7R_8$;

U is $CR_9$, oxygen, nitrogen, $NR_2$, $S(O)_n{}^*$, $C(=O)$, $C(=S)$ or $C(=NR_2)$;

When U is $CR_9$, E is nitrogen;

$R_1$ and $R_2$ are independent of each other and may be selected from the group consisting of hydrogen, $(C_{1-6})$alkyl, $(C_{2-6})$alkenyl, $(C_{2-6})$alkynyl, $(C_{1-6})$alkylcarbonyl, $(C_{-6})$cycloalkylcarbonyl, $(C_{1-6})$haloalkylcarbonyl, $(C_{1-6})$alkoxycarbonyl, arylcarbonyl and heteroarylcarbonyl, where any of these groups may be optionally substituted with one or more of the following groups consisting of halogen, hydroxy, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$ cycloalkyl, $R_3$, $R_4$, $R_5$, $R_6$, $R_7$, $R_8$ and $R_9$ are independent of each other and may be selected from the group consisting of hydrogen, halogen, hydroxy, mercapto, amino, cyano, nitro, $(C_{1-6})$alkyl, $(C_{1-6})$haloalkyl, $(C_{1-6})$alkoxy, $(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl, $(C_{1-6})$alkylamino, arylsulfonylamino, arylamino, $(C_{1-6})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxy, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, haloaryl, alkoxyaryl, aryoxy, arylthio, haloaryloxy, heteroaryl, heteroaryloxy and $(C_{3-7})$cycloalkyl;

n* is represent an integer from 0 to 2;

Q is selected from;

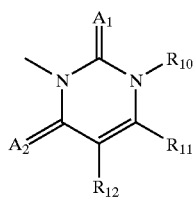

Q₁

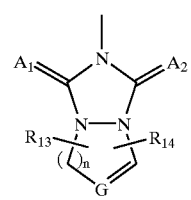

Q₂

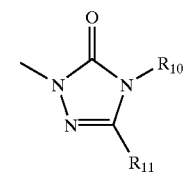

Q₃

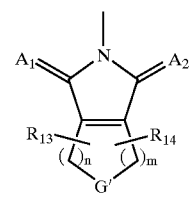

Q₄

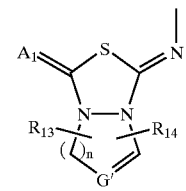

Q₅

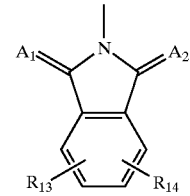

Q₆

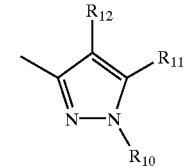

Q₇

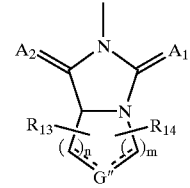

Q₈

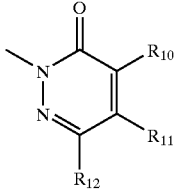

Q₉

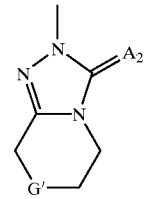

Q₁₀

Q11 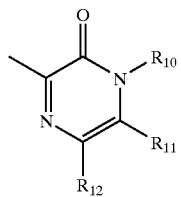

Q12 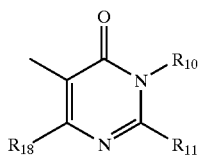

Q13 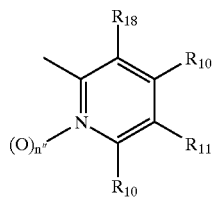

Q14 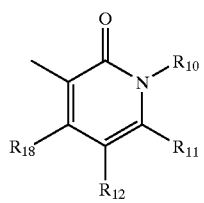

Q15 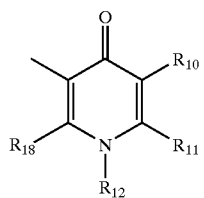

Q16 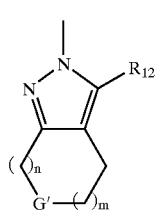

Q17 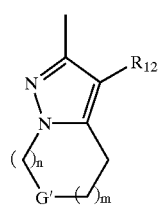

Q18 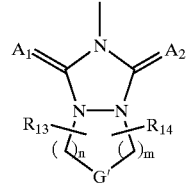

Q19 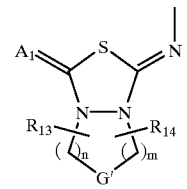

wherein $A_1$ and $A_2$ are independently oxygen or sulfur;

$R_{10}$ is hydrogen, halogen, cyano, nitro, formyl, $(C_{1-4})$alkyl, $(C_{1-4})$haloalkyl, amino, $(C_{1-4})$alkylamino, $(C_{1-4})$haloalkylamino, $(C_{1-4})$alkoxyamino, $(C_{1-4})$haloalkoxyamino, $(C_{1-4})$alkylcarbonyl, $(C_{1-4})$haloalkylcarbonyl, $(C_{1-4})$haloalkoxycarbonyl, $(C_{1-4})$alkylcabonylamino, $(C_{1-4})$haloalkylcarbonylamino, $(C_{1-4})$alkoxycarbonylamino, $(C_{1-4})$haloalkoxycarbonylamino, $(C_{1-6})$alkoxyalkyl, $(C_{1-6})$haloalkoxyalkyl, $(C_{1-6})$alkylthio, $(C_{1-4})$haloalkylthio, $(C_{2-6})$alkenyl, $(C_{2-4})$haloalkenyl, $(C_{2-6})$alkynyl or $(C_{2-6})$haloalkynyl;

$R_{11}$, $R_{12}$ and $R_{18}$ are independent of each other and may be selected from the group consisting of hydrogen, halogen, cyano, $(_{1-4})$alkyl, $(_{1-4})$haloalkyl, $(C_{1-4})$alkoxy, $(C_{1-4})$haloalkoxy, $(C_{2-6})$alkenyl, $(C_{2-6})$haloalkenyl, hydroxy or amino which may be optionally substituted with $(C_{1-4})$alkyl and $(C_{1-4})$haloalkyl;

$R_{13}$ and $R_{14}$ are independent of each other and may be selected from the group consisting of hydrogen, halogen, $(C_{1-3})$alkyl, $(C_{1-3})$haloalkyl, hydroxy, $(C_{1-3})$alkoxy, $(C_{1-3})$haloalkoxy, cyano, nitro, amino or $(C_{1-6})$alkylamino, When $R_{13}$ and $R_{14}$ are taken together with the atoms to which they are attached, they represent a three to seven membered substituted or unsubstituted ring optionally containing oxygen, $S(O)_n$*** or nitrogen with following optional substitutions, one to three halogen, cyano, nitro, hydroxy, amino, carbonyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl. $(C_{1-6})$haloalkylsulfonyl, aryl, heteroaryl or $(C_{3-7})$cycloalkyl;

G is nitrogen or $CR_{16}$,

G' is $NR_{15}$, oxygen, $S(O)_n$*** or $CR_{16}R_{17}$,

G" is nitrogen, $CR_{16}$, $NR_{15}$ oxygen, $S(O)_n$... or $CR_{16}R_{17}$ $R_{15}$ may be selected from the group consisting of hydrogen, $(C_{1-6})$alkyl, $(C_{1-6})$alkylcarbonyl, $(C_{1-6})$haloalkylcarbonyl, arylcarbonyl and heteroarylcarbonyl; where any of these groups may be optionally substituted with one or more of the following groups consisting of halogen, hydroxy, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl $R_{16}$ and $R_{17}$ are independent of each other and may be selected from the group consisting of hydrogen, halogen, hydroxy, mercapto, amino, cyano, $(C_{1-6})$alkyl, $(C_{1-6})$haloalkyl, $(C_{1-6})$alkoxy, $(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl,$(C_{1-6})$alkylamino, arylsulfonylamino, arylamino, $(C_{1-3})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;

n and m are independent of each other and represent an integer from 0 to 2; provided that m+n is 2, 3 or 4, $n^{}$ is 0 or 1, $n^{*}$ is represent an integer from 0 to 2, When Q is $Q_1$, $Q_3$, $Q_4$, $Q_{13}$, $Q_{18}$ or $Q_{19}$, structure (Ib) is excluded, When Q is $Q_7$, U is $CR_9$, nitrogen, $NR_2$, C(=O), C(=S) or C(=NR$_2$), Preferred compounds for the reasons of greater herbicidal efficacy are represented by formula (Ia) and (Ib) where X, Y are independent of each other and are represented by hydrogen, halogen or cyano;

A is oxygen, nitrogen, $NR_1$;

D is nitrogen or $NR_2$;

M is nitrogen or $NR_2$,

E and L are independent of each other and may be selected from $CR_7$, $CR_8$, $CR_7R_8$, oxygen, nitrogen, $S(O)_n{}^*$, C(=O), C(=S), C(=NR$_7$) or $CNR_7R_8$;

U is oxygen, nitrogen, $NR_2$ or $S(O)_n{}^*$;

$R_1$ and $R_2$ are independently of each other and may be selected from the group consisting of hydrogen, $(C_{1-6})$alkyl, $(C_{2-6})$alkenyl, $(C_{2-6})$alkynyl, $(C_{1-6})$alkylcarbonyl, $(C_{-6})$cycloalkylcarbonyl, $(C_{1-6})$haloalkylcarbonyl, arylcarbonyl and heteroarylcarbonyl, where any of these groups may be optionally substituted with one or more of the following groups consisting of halogen, hydroxy, mercapto, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, haloaryl, alkoxyaryl, heteroaryl and $(C_{3-7})$cycloalkyl;

$R_3$, $R_4$, $R_5$, $R_6$, $R_7$, $R_8$ and $R_9$ are independent of each other and may be selected from the group consisting of hydrogen, halogen, hydroxy, mercapto, amino, cyano, $(C_{1-6})$alkyl, $(C_{1-6})$haloalkyl, $(C_{1-6})$alkoxy, $(C_{1-6})$haloalkoxy, $(C_{1-6})$alkoxyalkyl, $(C_{2-6})$alkynyl , $(C_{2-6})$alkenyl, aryl, heteroaryl, aryloxy, heteroaryloxy, $(C_{3-6})$cycloalkyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl , $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl, $(C_{1-6})$alkylamino, arylsulfonylamino, arylamino, $(C_{1-3})$alkylthio, arylthio, $(C_{2-6})$alkenylthio, $(C_{2-6})$alkynylthio, $(C_1)$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be non-substituted or substituted with any of the functional groups represented by one more of the following halogen, hydroxy, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, aryloxy, heteroaryl heteroaryloxy and $(C_{3-7})$cycloalkyl, $n^*$ is represent an integer from 0 to 2, When Q is $Q_1$ or $Q_3$ stricture (Ib) is excluded, When Q is $Q_7$, U is nitrogen or $NR_2$, Q is selected from $Q_1$, $Q_2$, $Q_3$, $Q_7$, $Q_9$, $Q_{10}$, $Q_{16}$ or $Q_{17}$, wherein $A_1$ and $A_2$ are independently oxygen or sulfur, $R_{10}$ is $(C_{1-3})$alkyl, $(C_{1-3})$haloalkyl or amino $R_{11}$, $R_{12}$ are independent of each other and may be selected from the group consisting of hydrogen, halogen, cyano, $(C_{1-4})$alkyl, $(C_{1-4})$haloalkyl, $(C_{1-4})$alkoxy, $(C_{1-4})$haloalkoxy, $(C_{2-4})$alkenyl, $(C_{2-4})$haloalkenyl, hydroxy or amino which may be substituted with $(C_{1-4})$alkyl or $(C_{1-4})$haloalkyl;

$R_{13}$ and $R_{14}$ are independently of each other and may be selected from the group consisting of hydrogen, halogen, $(C_{1-3})$alkyl, $(C_{1-3})$haloalkyl, hydroxy, $(C_{1-3})$alkoxy, $(C_{1-3})$haloalkoxy, cyano, nitro, amino and $(C_{1-6})$alkylamino;

G is nitrogen or $CR_{16}$,;

G' is $NR_{15}$, oxygen, $S(O)_n{}^{***}$ or $CR_{16}R_{17}$, $R_{,5}$ may be selected from the group consisting of hydrogen, $(C_{1-6})$alkyl, $(C_{1-6})$alkylcarbonyl, $(C_{1-6})$haloalkylcarbonyl, arylcarbonyl and heteroarylcarbonyl, $R_{16}$ and $R_{17}$ are independent of each other and may be selected from the group consisting of hydrogen, halogen, hydroxy, mercapto, amino, cyano, $(C_{1-6})$alkyl, ($C_{1-6}$)haloalkyl, ($C_{1-6}$)alkoxy,($C_{1-6}$)haloalkoxy, ($C_{1-6}$) alkoxyalkyl, ($C_{2-6}$)alkynyl, ($C_{2-6}$)alkenyl, aryl, heteroaryl, aryloxy, heteroaryloxy, ($C_{3-6}$)cycloalkyl, carboxy, ($C_{1-6}$)alkylcarbonyl, arylcarbonyl, ($C_{1-3}$) haloalkylcarbonyl, ($C_{1-6}$)alkylcarbonyloxy, ($C_{1-6}$) haloalkylcarbonyloxy, ($C_{1-6}$)alkoxycarbonyl, ($C_{1-6}$) haloalkoxycarbonyl, ($C_{1-6}$)alkylthiocarbonyl, ($C_{1-6}$) haloalkylthiocarbonyl, ($C_{1-6}$)alkoxythiocarbonyl, ($C_{1-6}$)haloalkoxythiocarbonyl, ($C_{1-6}$)alkylamino, arylsulfonylamino, arylamino, ($C_{1-3}$)alkylthio, arylthio, ($C_{2-6}$)alkenylthio, ($C_{2-6}$)alkynylthio, ($C_{1-6}$) alkylsulfinyl, ($C_{2-6}$)alkenylsulfinyl, ($C_{2-6}$) alkynylsulfinyl, ($C_{1-6}$)alkylsulfonyl, ($C_{2-6}$) alkenylsulfonyl, ($C_{2-6}$)alkynylsulfonyl, arylsulfonyl, where any of these groups may be non-substituted or substituted with any of the functional groups represented by one more of the following halogen, hydroxy, cyano, nitro, amino, caboxyl, ($C_{1-6}$)alkyl, ($C_{1-6}$) haloalkyl, ($C_{1-6}$)alkylcarbonyl, ($C_{1-6}$) alkylcarbonyloxy, ($C_{1-6}$)haloalkylcarbonyl, ($C_{1-6}$) haloalkylcarbonyloxy, ($C_{1-6}$)alkoxy, ($C_{1-6}$) alkoxycarbonyl, aminocarbonyl, ($C_{1-6}$) alkylaminocarbonyl, ($_{1-6}$)haloalkoxy, ($C_{1-6}$) haloalkoxycarbonyl, ($C_{1-6}$)alkylsulfonyl, ($C_{1-6}$) haloalkylsulfonyl, aryl, heteroaryl and ($C_{3-7}$)cycloalkyl n and m are independent of each other and represent an integer from 0 to 2; provided that m+n=2 or 3;

n** is 0 or 1;

n*** is represent an integer from 0 to 2.

Certain compounds of present invention are novel. These are represented by the following formula.

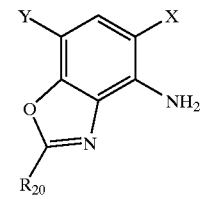
a

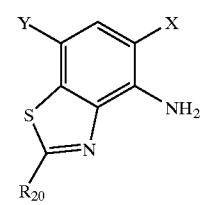
b

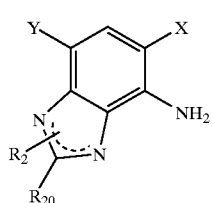
c

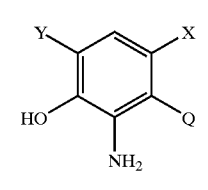
d

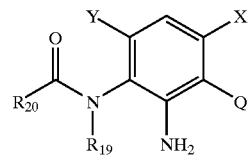
e

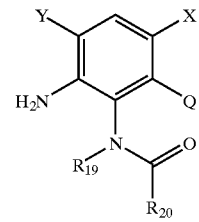
f in which

X is hydrogen or halogen;

Y is halogen, cyano, nitro, ($C_{1-3}$)haloalkyl, or ($C_{1-3}$) alkoxyalkyl;

Q is $O_1$, $Q_2$, $Q_3$, $Q_7$, $Q_9$, $Q_{10}$, $Q_{16}$ or $Q_{17}$;

$R_{19}$ is hydrogen, ($C_{1-6}$)alkyl, ($C_{1-6}$)alkylcarbonyl, ($C_{1-6}$) haloalkylcarbonyl, arylcarbonyl, heteroarylcarbonyl;

where any of these groups may be optionally substituted with one or more of the following groups consisting of halogen, hydroxy, cyano, nitro, amino, caboxyl, ($C_{1-6}$) alkyl, ($C_{1-6}$)haloalkyl, ($C_{1-6}$)alkylcarbonyl, ($C_{1-6}$) alkylcarbonyloxy, ($C_{1-6}$)haloalkylcarbonyl, ($C_{1-6}$) haloalkylcarbonyloxy, ($C_{1-6}$)alkoxy, ($C_{1-6}$) alkoxycarbonyl, aminocarbonyl, ($C_{1-6}$) alkylaminocarbonyl, ($C_{1-6}$)haloalkoxy, ($C_{1-6}$) haloalkoxycarbonyl, ($C_{1-6}$)alkylsulfonyl, ($C_{1-6}$) haloalkylsulfonyl, aryl, heteroaryl and ($C_{3-7}$) cycloalkyl;

$R_{20}$ is selected from the group consisting of hydrogen, halogen, hydroxy, mercapto, amino, cyano, ($C_{1-6}$)alkyl, ($C_{1-6}$)haloalkyl, ($C_{1-6}$)alkoxy, ($C_{1-6}$)haloalkoxy, ($C_{1-6}$) alkoxyalkyl, ($C_{2-6}$)alkynyl, ($C_{2-6}$)alkenyl, aryl, heteroaryl, aryloxy, heteroaryloxy, ($C_{3-6}$)cycloalkyl, carboxy, ($C_{1-6}$)alkylcarbonyl, arylcarbonyl, ($C_{1-3}$) haloalkylcarbonyl, ($C_{1-6}$)alkylcarbonyloxy, ($C_{1-6}$) haloalkylcarbonyloxy, ($C_{1-6}$)alkoxycarbonyl, ($C_{1-6}$) haloalkoxycarbonyl, ($C_{1-6}$)alkylthiocarbonyl, ($C_{1-6}$) haloalkylthiocarbonyl, ($C_{1-6}$)alkoxythiocarbonyl, ($C_{1-6}$)haloalkoxythiocarbonyl, ($C_{1-6}$)alkylamino, arylsulfonylamino, arylamino, ($C_{1-6}$)alkylthio, arylthio, ($C_{2-6}$)alkenylthio, ($C_{2-6}$)alkynylthio, ($C_{1-6}$) alkylsulfinyl, ($C_{2-6}$)alkenylsulfinyl, ($C_{2-6}$) alkynylsulfinyl, ($C_{1-6}$)alkylsulfonyl, ($C_{2-6}$) alkenylsulfonyl, ($C_{2-6}$)alkynylsulfonyl, arylsulfonyl, where any of these groups may be non-substituted or substituted with any of the functional groups represented by one more of the following, halogen, hydroxy, cyano, nitro, amino, caboxyl, ($C_{1-6}$)alkyl, ($C_{1-6}$) haloalkyl, ($C_{1-6}$)alkylcarbonyl, ($C_{1-6}$) alkylcarbonyloxy, ($C_{1-6}$)haloalkylcarbonyl, ($C_{1-6}$) haloalkylcarbonyloxy, ($C_{1-6}$)alkoxy, ($C_{1-6}$) alkoxycarbonyl, aminocarbonyl, ($C_{1-6}$) alkylaminocarbonyl, ($C_{1-6}$)haloalkoxy, ($C_{1-6}$) haloalkoxycarbonyl, ($C_{1-6}$)alkylsulfonyl, ($C_{1-6}$) haloalkylsulfonyl, aryl, heteroaryl and ($C_{3-7}$) cycloalkyl.

In the definitions given above, unless alkyl, alkenyl and halogen are defined or mentioned, the term alkyl used either alone or in compound words such as "haloalkyl" or "alkylcarbonyl" includes straight-chain or branched chains containing 1 to 6 carbon atoms. The terms of alkenyl and alkynyl include straight chain or branched alkenes and alkynes respectively containing 2 to 6 carbon atoms, and the term halogen either alone or in the compound words such as haloalkyl indicates fluorine, chlorine, bromine, or iodine. Further a haloalkyl is represented by an alkyl partially or filly substituted with halogen atoms which may be same or different. The term or part of the term "aryl" or "heteroaryl" are defined as those monocyclic or fused bicyclic aromatic rings wherein at least one ring satisfy the Hückel rule and contain 0 to 4 heteroatoms, examples include: phenyl, furyl, furazanyl, thienyl, pyrrolyl, pyrazolyl, oxazolyl, oxadiazolyl, imidazolyl, isoxazolyl, thiazolyl, thiadiazolyl, isothiazolyl, tetrazolyl, pyridinyl, pyrimidinyl, pyridazinyl, pyrazinyl, triazinyl, quinolyl, isoquinolyl, quinoxalinyl, benzofuranyl, 2,3-dihydrobenzofuranyl, isobenzofuranyl, benzothienyl, benzodioxolyl, chromanyl, indolinyl, isoindolyl, naphthyl, thienofuranyl and purinyl. These rings can attached through any available carbon or nitrogen, for example, when the aromatic ring system is furyl, it can be 2-furyl or 3-furyl, for pyrrolyl, the aromatic ring system is 1-pyrrolyl, 2-pyrrolyl or 3-pyrrolyl, for naphthyl, the carbobicyclic aromatic ring is 1-naphthyl or 2- naphthyl and for benzofuranyl, the aromatic ring system can be 2-, 3-, 4-, 5-, 6- or 7-benzofuranyl.

DETAILED DESCRIPTION OF THE INVENTION

The compounds described by the Formula (Ia) and (Ib) can be prepared by the procedures as described herein. Using commercially available starting materials or those whose synthesis is known in the art. the compounds of this invention may be prepared using methods described in the following Schemes, or using modifications thereof which are within the scope of the art. The starting phenol represented by formula II in Scheme 1 can be nitrated according to the literature procedure (WO 9722618). The reaction is accomplished by treatment with nitric acid at a temperature between −30° C. and 50° C. for 0.5–12 hours. The reaction solution is poured into ice-water, then isolated and purified. IV can be prepared by the reduction of III typically by treatment with iron in an acidic medium such as acetic acid or catalytic hydrogenation at a temperature between 0° C. and 50° C. for 1–24 hours. IV can be treated with acid chloride or acid anhydride in the presence of base such as trimethyl amine or acid such as pyridinium p-toluensulfonate (PPTS) in an inert solvent such as m-xylene at 20–250° C. for 1–24 hours to give benzoxazole type compound represented by formula V. These compounds can be nitrated with a nitration reagent such as nitric acid at a temperature between −10° C. and 50° C. for 0.5–12 hours. The reaction solution is poured into ice-water followed by filtration. VI can be obtained as a mixture with its regio-isomer represented by formula VII.

The reduction of VI to amine derivatives represented by formula VIII can be carried out by treatment with iron in an acidic medium such as acetic acid or by catalytic hydrogenation at a temperature between 0° C. and 30° C. for 1–24 hours. Further modification from VIII to IX can be carried out as described in this patent.

SCHEME 1

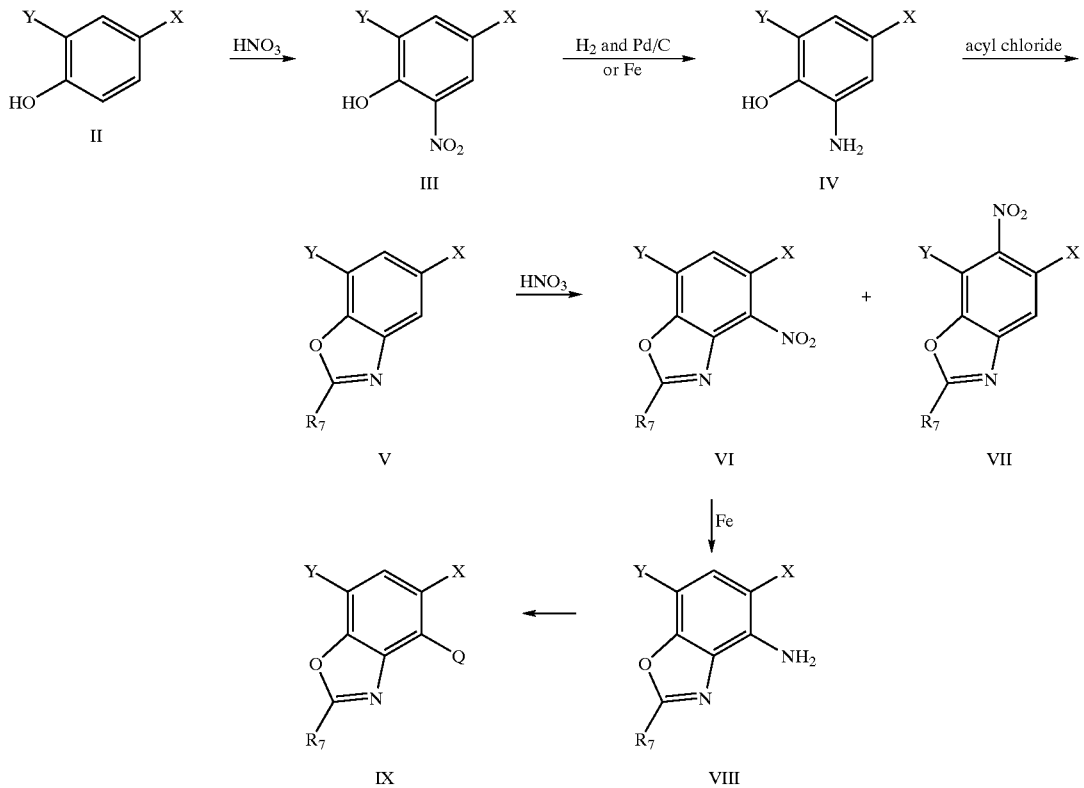

The phthalimide derivative represented by formula XI can be prepared by the treatment of X with phthalic anhydride in an acidic medium such as acetic acid at a temperature between 30° C. and 200° C. for 1–24 hours.

Nitration can be carried out by its addition to a mixture of sulfuric acid and nitric acid at a temperature between −15° C. and 50° C. for 0.5–12 hours followed by addition of ice-water to give the desired compound represented by formula XII. XII can be deprotected to give amine derivatives represented by formula XIII. Removal of the protecting group can be accomplished using several methods. such as treatment with hydrazine in a polar solvent such as dimethylsulfoxide (DMSO) or by treatment with an organic amine such as methyl amine in ethanol. Amino group of XIII can be derived to XIV as described in this patent.

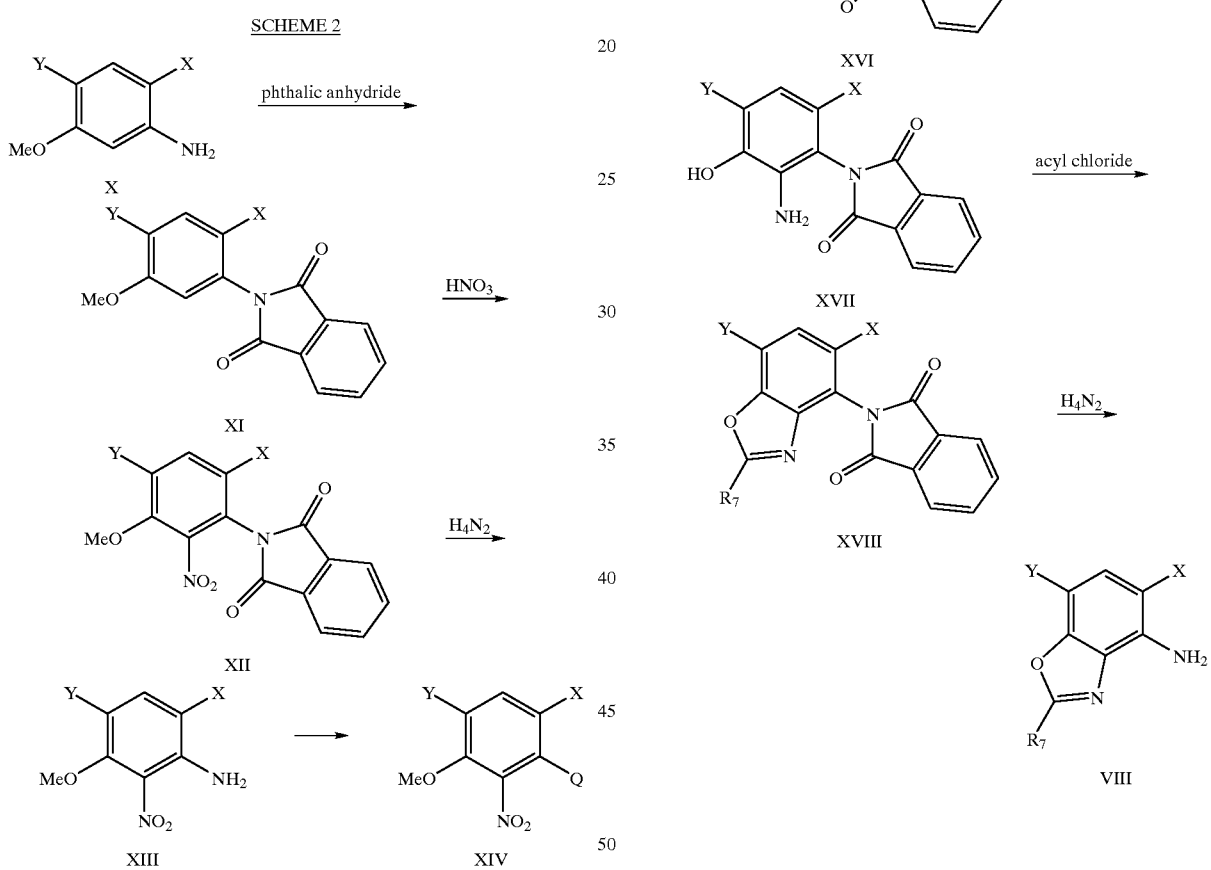

Phthalimide derivative represented by the formula XV in Scheme 3 can be prepared according to the literature procedure (WO 93/14073). Nitration can be carried out by treatment with a nitrating reagent such as nitric acid at a temperature between −30° C. and 30° C. for 0.5–12 hours. XVI is then converted into the corresponding amine represented by formula XVII by typical reduction procedures e.g. iron in an acidic medium such as acetic acid or by catalytic hydrogenation. Benzoxazole derivatives represented by formula XVIII can be prepared according to the general procedures described in Scheme 1. The phthalimide group can be removed according to the general procedure described in Scheme 2 to give VIII.

The product represented by formula XXII in Scheme 4 can be prepared analogously by known method (JP2-289573). Urea derivatives represented by formula XX can be prepared by a coupling reaction with the corresponding amine in an inert solvent such as ethyl acetate at a temperature between 0° C. and 30° C. for 1–12 hours. XXI can be prepared from XX by using diphosgene or related reagent such as triphosgene in an inert solvent such as dichloromethane at a temperature between 0° C. and 150° C. for 1–12 hours. The final compounds represented by formula XXII can be prepared from XX by treatment with a catalytic amount of base such as sodium methoxide in a polar solvent such as methanol at a temperature between 20° C. and 150° C. for 0.5–12 hours.

SCHEME 4

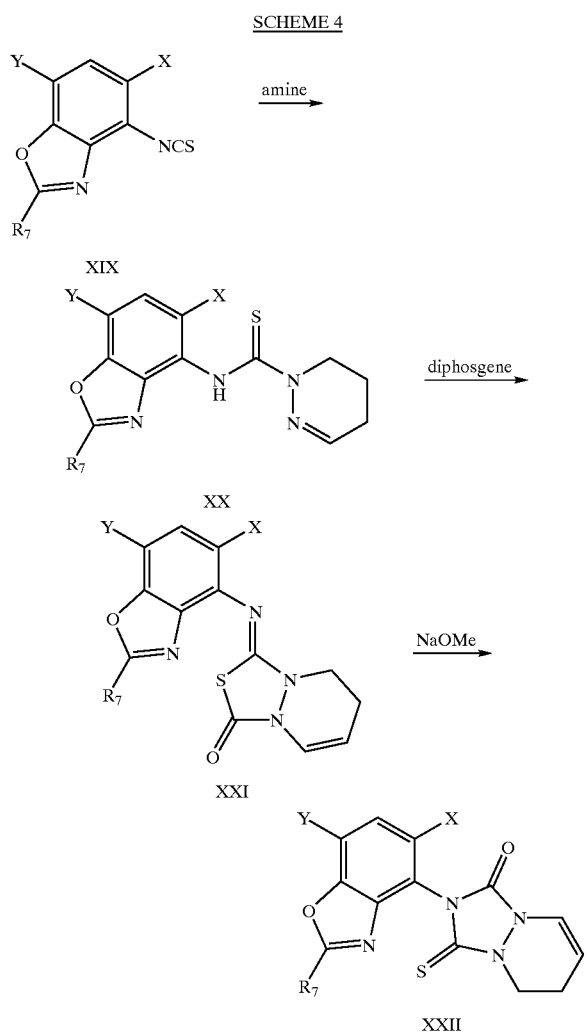

The product represented by the formula XXIII in Scheme 5 can be prepared analogously by known method (EP 688773). The reaction is carried out at a temperature between −78° C. and 100° C. for 0.5–24 hours in an inert solvent such as tetrahydrofuran (THF) or toluene.

SCHEME 5

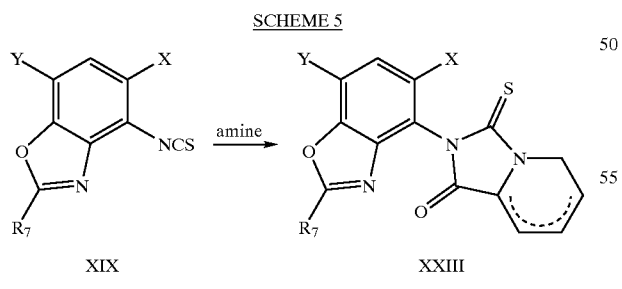

The compounds represented by formula XXV in Scheme 6 can be prepared from XXIV by treatment with 2-halo keto-derivatives such as phenacyl bromide in the presence of base such as potassium carbonate in an inert solvent such as acetone or acetonitrile. The reaction can be carried out at a temperature between 30° C. and 100° C. for 1–24 hours.

SCHEME 6

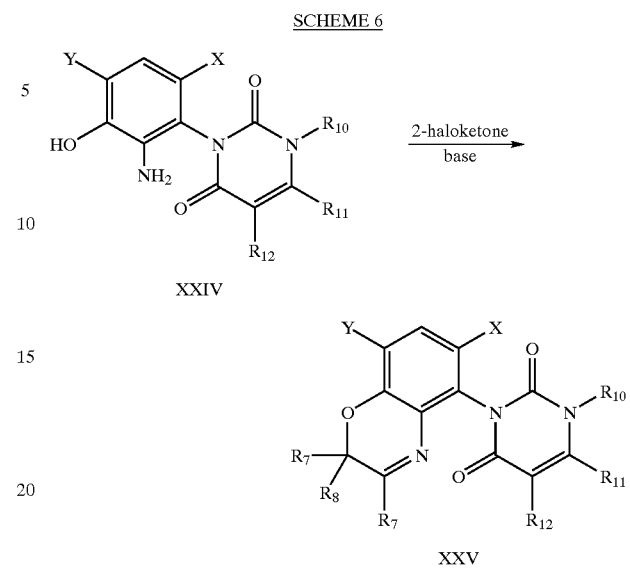

The compounds represented by formula XXVI in Scheme 7 can be prepared according to the procedure outlined by Y. Masuoka et al. in Chem Pharm. Bull 34(1) 130–139 (1986). The starting compound represented by formula XXIV was treated with allyl halide such as methyl 4-bromocrotonate in the presence of base such as sodium bicarbonate in a solvent such as methanol at a temperature between 0° C. and 100° C. for 1–24 hours

SCHEME 7

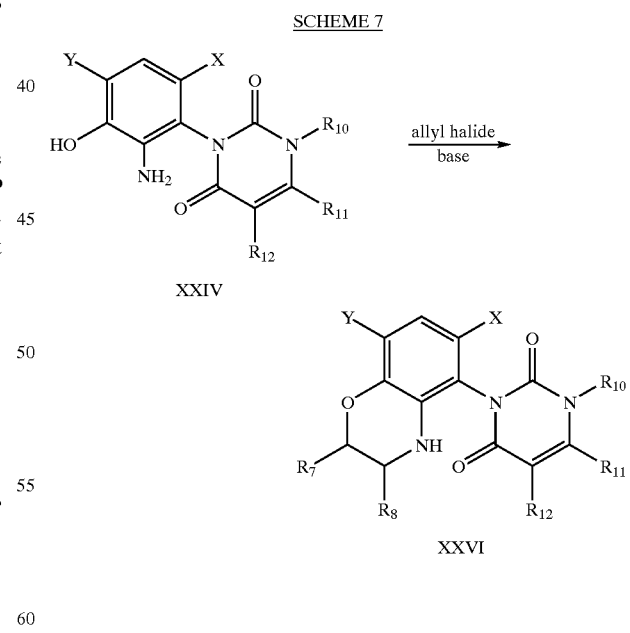

The product represented by formula XXVII in Scheme 8 can be prepared from XXIV by treatment with 1,2-dicarbonyl derivatives such as methyl pyruvate in an inert solvent such as toluene or THF. The reaction carried out at a temperature between 0° C. and 150° C. for 0.5–24 hours.

SCHEME 8

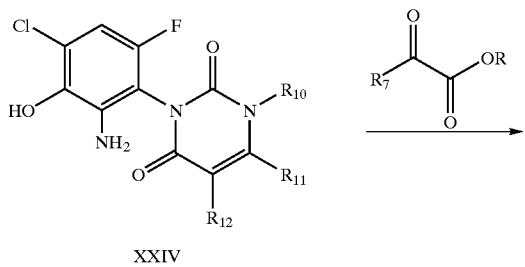

XXIV

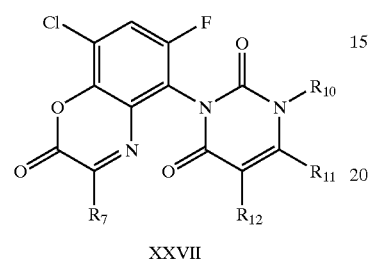

XXVII

The product represented by formula XXVIII in Scheme 9 can be prepared from XXIV by a cyclization reaction with 2-halogenated ester such as ethyl 2-bromopropionate. The reaction can be carried out in the presence of base such as potassium carbonate in a solvent such as acetonitrile at a temperature between 25° C. and 100° C. for 1–24 hours.

SCHEME 9

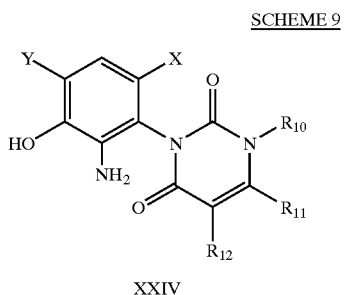

XXIV

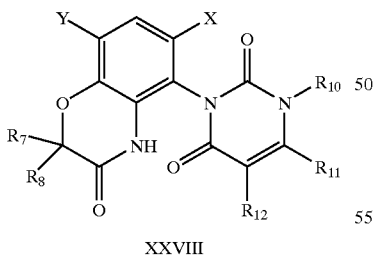

XXVIII

The compounds represented by formula XXVIII in Scheme 10 can be prepared from XXIV using 1,2-dihaloderivatives such as 1,2-dibromoethane in the presence of base such as potassium carbonate in an inert solvent such as acetone. The reaction is carried out at a temperature between 20° C. and 150° C. for 0.5–24 hours.

SCHEME 10

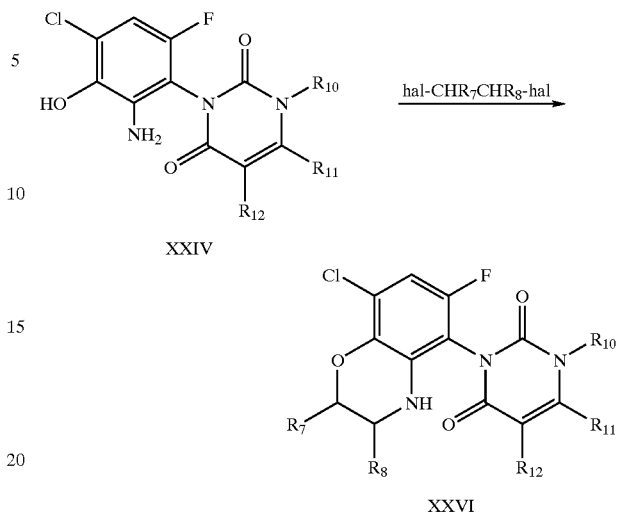

XXIV

XXVI

Aniline derivatives represented by formula XXIX in Scheme 11 can be converted to corresponding isocyanates represented by formula XXX, using phosgene or triphosgene in the presence of base such as triethylamine. The reaction can be carried out in an inert solvent such as ethyl acetate at a temperature between 0° C. and 100° C. for 0.5–24 hours. Uracil derivatives represented by formula XXI can be prepared analogously by known method (U.S. Pat. No. 4,859,229).

SCHEME 11

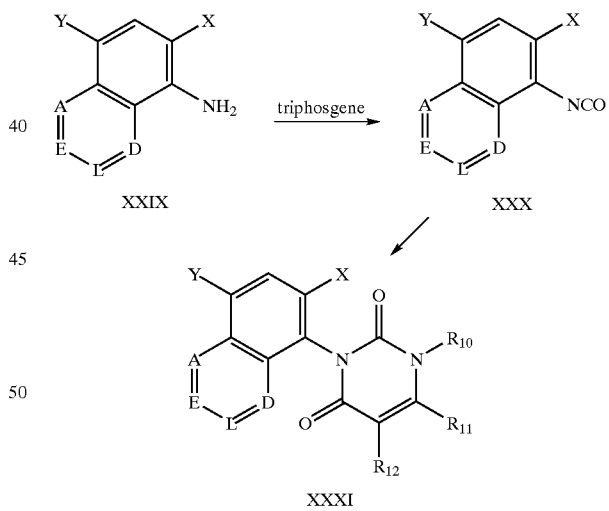

XXIX

XXX

XXXI

The starting pyrazole derivatives represented by formula XXXII in Scheme 12 can be nitrated with a nitrating reagent such as nitric acid in an acidic medium such as sulfuric acid at a temperature between −30° C. and 50° C. for 0.5–12 hours. Product (XXXIII) is isolated by addition of water and filtered. XXXIV can be prepared by the reduction of XXXIII typically by catalytic hydrogenation in the presence of catalysts such as palladium on carbon or by treatment with iron in an acidic medium such as acetic acid. Further modification of XXXIV to XXXV is carried out according to the general procedures described in Scheme 1.

SCHEME 12

XXXII → XXXIII

↓

XXXV ← XXXIV
(R<sub>7</sub>COCl)

The starting compounds represented by formula XXXVI in Scheme 13 can be prepared analogously by known method (WO97/07104). Nitration can be carried out with a nitrating reagent such as nitric acid in an acidic medium such as sulfuric acid at a temperature between −30° C. and 50° C. for 0.5–12 hours to give XXXVII. Aniline derivatives represented by formula XXXVIII can be prepared from XXXVII by treatment with iron in an acidic medium such as acetic acid or by catalytic hydrogenation. Further transformation through aminophenol represented by formula XXXIX to XL can be carried out following to the method described in Scheme 1.

SCHEME 13

XXXVI →(H$_2$SO$_4$/HNO$_3$) XXXVII →(Fe) XXXVIII →(BBr$_3$/SMe$_2$)

XXXIX → XL

The starting compounds represented by formula XLI in Scheme 14 can be prepared according to the literature procedure (WO97/07104). Nitration can be carried out with a nitrating reagent such as nitric acid. The reaction can be carried out at a temperature between −20° C. and 100° C. for 0.5–12 hours to give XLII. Aniline derivative represented by formula XLIII can be prepared from XLII by treatment with iron in an acetic medium such as acetic acid or by catalytic hydrogenation. Further transformation through aminophenol represented by formula XLIII to XLIV can be carried out following to the method described in Scheme I

SCHEME 14

XLI →(nitration) XLII →(Fe) XLIII → XLIV

The starting compound represented by formula XLV in Scheme 15 can be prepared following literature methods, such as U.S. Pat. No. 4,213,773. Nitration can be carried out with a nitrating reagent such as nitric acid with or without acidic medium such as sulfuric acid at a temperature between −20° C. and 50° C. for 0.5–24 hours to give XLVI. Aminophenol derivatives represented by formula XLVII can be prepared from XLVI by treatment with iron in an acidic medium such as acetic acid or by catalytic hydrogenation. The reaction can be carried out at a temperature between 0° C. and 100° C. for 1–48 hours. Benzoxazole derivatives represented by formula XLVIII can be prepared according to the general procedures described in Scheme 1.

SCHEME 15

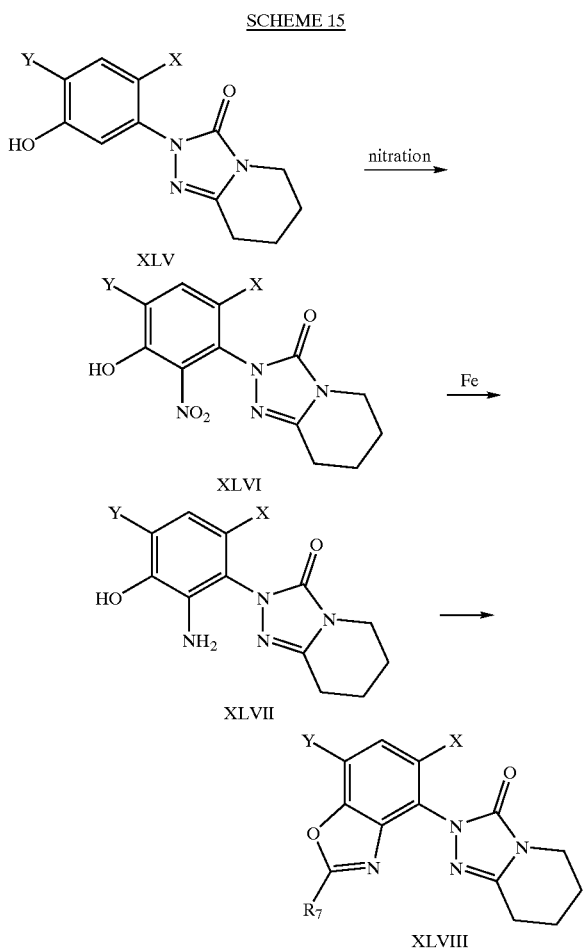

The starting compound represented by formula XLIX in Scheme 16 can be prepared following literature method (WO92/06962). Nitration can be carried out with a nitrating reagent such as nitric acid with or without acidic medium such as sulfuric acid at a temperature between −20° C. and 50° C. for 0.5–24 hours to give L. Aminophenol derivatives represented by formula LI can be prepared from L by treatment with iron in an acidic medium such as glacial acetic acid or by catalytic hydrogenation in the presence of catalyst such as palladium on carbon. The reaction can be carried out at a temperature between 0° C. and 100° C. for 1–48 hours. Further modification of LI to LII is carried out according to the general procedures described in Scheme 9.

SCHEME 16

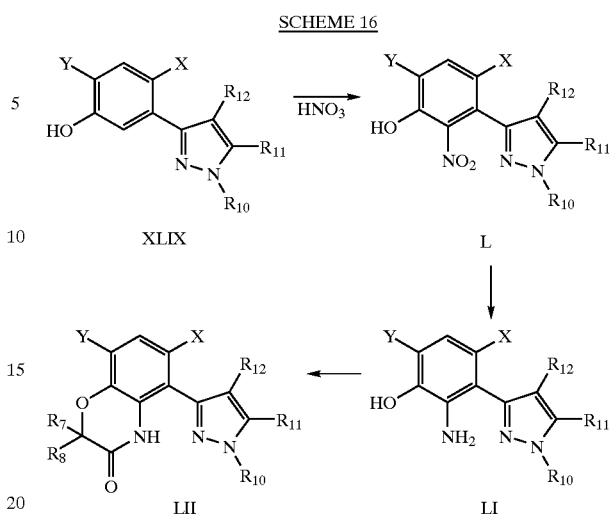

EXAMPLE 1

Preparation of 4-Amino-7-chloro-2-ethyl-5-fluorobenzoxazole (Compound no. 14-3)

Step 1 Preparation of 2-Chloro-4-fluoro-6-nitrophenol as an Intermediate.

2-Choro-4-fluorophenol (24 g) was slowly added to nitric acid (69%, 100 ml) at 0° C. The mixture was stirred for 20 minutes and then poured into ice-water (250 ml), the resulting yellow crystals were separated by filtration and washed with cold water, and dried in vacuum to afford the title compound (29 g). $^1$H-NMR (CDCl$_3$, 300 MHz): 7.53(1H, dd, J=3.0 Hz, 7.2 Hz), 7.79(1H, dd, J=3.1 Hz, 8.0 Hz), 10.78(1H, s) ppm.

Step 2 Preparation of 2-Amino-6-chloro-4-fluorophenol as an Intermediate.

2-Chloro-4-fluoro-6-nitrophenol (13.5 g) was dissolved in ethyl acetate (150 ml) containing palladium on activated carbon (10%, 1.35 g). The hydrogen was bubbled through the suspension for 16 hours. and the mixture was filtered. After evaporation of the solvent, the title compound was obtained as white crystals (10.4 g). $^1$H-NMR (CDCl$_3$, 300 MHz): 3.99(2H, br s), 5.28(1H, br s), 6.37(1H, dd, J=2.9 Hz, 9.8 Hz), 6.47(1H, dd, J=2.9 Hz, 8.3 Hz) ppm.

Step 3 Preparation of 7-Chloro-2-ethyl-5-fluorobenzoxazole as an intermediate

2-Amino-6-chloro-4-fluorophenol (3 g) was dissolved in m-xylene (150 ml) containing propionyl chloride (2.05 g), triethylamine (2.24 g) and pyridinium p-toluenesulfonate (2.8 g). The mixture was refluxed under N$_2$ for 4 hours, then cooled to room temperature and passed through a silica gel column eluted with a mixture of hexane and ether (5:1) to yield the title compound as a pale-brown solid (2.85 g). $^1$H-NMR (CDCl$_3$, 300 MHz): 1.45(3H, t, J=7.6 Hz), 2.98 (2H, q, J=7.6 Hz), 7.07(1 H, dd, J=2.3 Hz, 9.2 Hz), 7.27(1 H, dd, J=2.4 Hz, 8.1 Hz) ppm.

Step 4 Preparation of 7-Chloro-2-ethyl-5-fluoro-4-nitrobenzoxazole as an Intermediate 7-Chloro-2-ethyl-5-fluorobenzoxazole (0.9 g) was slowly added to a mixture of sulfuric acid (9 ml) and nitric acid (0.6 ml) at −40° C. The dryice-acetone bath was removed and the mixture stirred for 2 hours. Ice-water was added and the mixture was extracted with ether. The organic phase was dried over anhydrous sodium sulfate and concentrated to an oil under reduced pressure. The residue was purified by column chromatography on silica gel using 5% ether in hexane. The desired product was obtained as a white solid [0.35 g, $^1$H-NMR (CDCl$_3$, 300 MHz): 1.48(3H, t, J=7.6 Hz), 3.07(2H, q, J=7.6 Hz), 7.27(1H, d, J=10.5 Hz) ppm], along with a by-product, 7-chloro-2-ethyl-5-fluoro-6-nitrobenzoxazole (0.49 g).

Step 5 Palladium on activated carbon (10%, 0.1 g) was added to a solution of 7-chloro-2-ethyl-5-fluoro-4-nitrobenzoxazole (0.86 g) in ethyl acetate (80 ml) and hydrogen was bubbled through the suspension for 5 hours. After filtration and evaporation, 4-amino-7-chloro-2-ethyl-5-fluorobenzoxazole(0.73 g) was obtained as the single product.

EXAMPLE 2

Preparation of N-(2-t-butyl-7-Chloro-5-fluorobenzoxazol-4-yl)phthalimide (Compound no. 6-2)

Step 1 Preparation of N-(4-Chloro-2-fluoro-5-hydroxyphenyl)phthalimide as an Intermediate 5-Amino-2-chloro-4-fluorophenol (3.0 g) and phthalic anhydride (2.75 g) were dissolved in acetic acid (60 ml) and the solution was refluxed for 2 hours. After allowing it to cool to ambient temperature, the solution was added to water and the precipitate was separated by filtration to furnish the title compound (5.04 g). $^1$H NMR (CDCl$_3$+CD$_3$OD, 300 MHz) 3.68 (1H, s), 6.93 (1H, d, J=6.6 Hz), 7.27 (1H, d, J=9.1 Hz), 7.84 (2H, dd, J=3.0, 5.5 Hz), 7.97 (2H, dd, J=3.0, 5.5 Hz) ppm.

Step 2 Preparation of N-(4-Chloro-6-fluoro-3-hydroxy-2-nitrophenyl)phthalimide as an Intermediate Powdered N-(4-chloro-2-fluoro-5-hydroxyphenyl) phthalimide (5.0 g) was slowly added to stirred HNO$_3$ (69%) at −10 ° C. The solution was slowly warmed to room temperature and allowed to stir for 0.5 hour. The solution was then added to ice water and resultant precipitate was separated by filtration to afford the title compound (5.5 g). $^1$H NMR (CDCl$_3$+CD$_3$OD, 300 MHz) 4.36 (1H, br s), 7.61 (1H, d, J=8.6 Hz), 7.88 (2H, dd, J=3.0, 5.5 Hz), 7.99 (2H, dd, J=3.0, 5.5 Hz) ppm.

Step 3 Preparation of N-(2-Amino-4-chloro-6-fluoro-3-hydroxyphenyl)phthalimide as an Intermediate N-(4-Chloro-6-fluoro-3-hydroxy-2-nitrophenyl) phthalimide (5.5 g) was dissolved in glacial acetic acid (55 ml) and iron powder (3.64 g) was slowly added. The solution was stirred at ambient temperature overnight. Water was added and the product extracted with ethyl acetate. The organic layer was washed with saturated sodium bicarbonate solution followed by water. Solvent was removed under reduced pressure to afford the title compound (4.86 g). $^1$H NMR (CDCl$_3$, 300 MHz) 5.42 (1H, br s), 6.58 (1H, d, J=9.4 Hz), 7.95 (4H, m) ppm.

Step 4 Preparation of N-(2-t-butyl-7-Chloro-5-fluorobenzoxazol-4-yl)phthalimide as an Intermediate A solution of N-(2-amino-4-chloro-6-fluoro-3-hydroxyphenyl)phthalimide (2 g), triethylamine (0.79 g), pyridinium p-toluenesulfonate (0.99 g), and pivaloyl chloride (0.95 g) in m-xylene (65 ml) was refluxed for 8 hours. Solvent was then evaporated under reduced pressure and the product was subjected to silica gel chromatography. N-(2-t-butyl-7-chloro-5-fluorobenzoxazol-4-yl)phthalimide was eluted with methylene chloride as the eluent (2.17 g).

EXAMPLE 3

Preparation of 8-(7-Chloro-2-ethyl-5-fluorobenzoxazol-4-yl)-1,6,8-triazabicyclo[4,3,0]2-nonene-9-one-7-thione (Compound no. 8-1)

Step 1 Preparation of 1-(7-Chloro-2-ethyl-5-fluorobenzoxazol-4-yl-thiocarbamoyl)-1,4,5,6-tetrahydropyridazine as an Intermediate 1,4,5,6-Tetrahydropyridazine (0.3 g) and an equivalent of 7-chloro-2-ethyl-5-fluoro-4-isothiocyanobenzoxazole (preparation given in Example 15, Step 1) were mixed in THF (30 ml) and the mixture was stirred for 3 hours. Following evaporation of solvent, the residue was purified by column chromatography on silica gel using hexane-ethyl acetate (1:1) to afford 0.36 g of the title compound. $^1$H-NMR (CDCl$_3$, 300 MHz): 1.42(3H, t, J=7.5 Hz), 1.97(2H, m), 2.28(2H, m), 2.97(2H, q, J=7.6 Hz), 4.36(2H, m), 7.01(1H, m), 7.16(1H, d, J=10.0 Hz), 9.30(1H, s) ppm.

Step 2 Preparation of 9-(7-Chloro-2-ethyl-5-fluorobenzoxazol-4-yl-imino)-8-thia-1,6-diazabicyclo[4,3,0]4-nonene-7-one as an Intermediate 1-(7-Chloro-2-ethyl-5-fluorobenzoxazol-4-yl-thiocarbamoyl)-1,4,5,6-tetrahydropyridazine (0.33 g) was dissolved in methylene chloride (5 ml). The mixture was cooled in a dry ice/acetone bath (−20° C.) and stirred during addition of pyridine (0.23 g) and diphosgene (0.09 ml). After removal of the cooling bath, the mixture was stirred for an additional 4 hours, followed by column chromatographic purification on silica gel using hexane-ethyl acetate (3:1) to give 0.2 g of the title compound. $^1$H-NMR (CDCl$_3$, 300 MHz): 1.44(3H, t, J=7.5 Hz), 2.54(2H, m), 2.98(2H, q, J=7.6 Hz), 4.21(2H, t, J=5.8 Hz), 5.36(1H, m), 6.93(1H, d, J=8.3 Hz), 7.13(1H, d, J=10.6 Hz) ppm.

Step 3 9-(7-Chloro-2-ethyl-5-fluorobenzoxazol-4-yl-imino)-8-thia-1,6-diazabicyclo[4,3,0]4-nonene-7-one (0.14 g) was dissolved in methanol (10 ml) containing sodium methoxide (0.03 g). The mixture was refluxed for 0.5 hour. After evaporation of solvent, the residue was purified by passing through a silica gel column eluting by ether to give 8-(7-chloro-2-ethyl-5-fluorobenzoxazol-4-yl)-1,6,8-triazabicyclo[4,3,0]2-nonene-9-one-7-thione (0.14 g).

EXAMPLE 4

Preparation of 8-(7-Chloro-2-ethyl -5-fluorobenzoxazol-4-yl)-1,8-diazobicyclo[4,3,0] nonane-7-one-9-thione (Compounds no. 7-5 and 7-6)

Ethyl pipecolinate (0.51 g) was mixed with an equivalent of 7-chloro-2-ethyl-5-fluoro-4-isothiocyanobenzoxazole (preparation given in Example 20, Step 1) in ethyl acetate (25 ml), and the resulting mixture stirred for 16 hours. After the solvent was evaporated, the residue was purified by column chromatography on silica gel using hexane-ethyl acetate (3:1) to give two diastereomers of the product (0.4 g in total).

EXAMPLE 5

Preparation of 3-(8-Chloro-6-fluoro-3-phenyl-2H-1,4-benzoxazin-5-yl)-1-methyl-6-trifluoromethyl-2,4 (1H,3H)-pyrimidindione (Compound no. 1-3)

A mixture of 3-(2-amino-4-chloro-6-fluoro-3-hydroxyphenyl)-1-methyl-6-trifluoromethyl-2,4(1H,3H)-pyrimidinedione (0.5 g), phenacyl bromide (0.29 g) and potassium carbonate (0.2 g) in acetone (30 ml) was stirred under reflux conditions for 1 hour. Then insoluble salt was removed through Celite and the filtrate concentrated under reduced pressure. The oily substance was purified by column chromatography on silica gel using ethyl acetate-hexane(1:4) as eluent to give the title compound (0.12 g).

EXAMPLE 6

Preparation of 3-[8-Chloro-6-fluoro-2-(methoxycarbonyl)methyl-3,4-dihydro-2H-1,4-benzoxazin-5-yl]-1-methyl-6-trifluoromethyl-2,4(1H,3H)-pyrimidindione (Compound no. 2-8)

A mixture of 3-(2-amino-4-chloro-6-fluoro-3-hydroxyphenyl)-1-methyl-6-trifluoromethyl-2,4(1H,3H)-pyrimidinedione (0.43 g), methyl 4-bromocrotonate (0.22 g) and sodium bicarbonate (0.3 g) in methanol was stirred at 25° C. for 12 hours. The solvent was removed under reduced pressure and ethyl acetate (200 ml) was added. The organic phase was washed with saturated brine, dried over anhydrous sodium sulfate and concentrated to an oil. The crude product was purified by column chromatography on silica gel using ethyl acetate-hexane (1:2) as eluent to give title compounds (0.097 g)

EXAMPLE 7

Preparation of 3-(8-Chloro-6-fluoro-3-methyl-2H-1,4-benzoxazin-2-one-5-yl)-1-methyl-6-trifluoromethyl-2,4(1H,3H)-pyrimidindione (Compound no. 3-1)

3-[7-Chloro-5-fluoro-2(3H)benzoxazolinon-4-yl]-1-methyl-6-trifluoromethyl-2,4(1H,3H)-pyrimidinedione (0.50 g) was dissolved in anhydrous toluene (15 ml) and methyl pyruvate (0.15 g) was added. The solution was refluxed with azeotropic removal of water for 2 hours and the solvent was then removed under reduced pressure. The residue was chromatographed on silica gel using hexane-ethyl acetate (3:1) as the eluent to afford the title compound (0.23 g).

EXAMPLE 8

Preparation of 3-(8-Chloro-6-fluoro-2-methyl-2H-1,4-benzoxazin-3-one-5-yl)-1-methyl-6-trifluoromethyl-2,4(1H,3H)-pyrimidindione (Compound no. 4-3)

A mixture of 3-(2-amino-4-chloro-6-fluoro-3-hydroxyphenyl)-1-methyl-6-trifluromethyl-2,4(1H,3H)-pyrimidinedione (1.07 g), ethyl bromopropionate (0.61 g) and potassium carbonate (0.414 g) in acetonitrile (30 ml) was stirred at room temperature overnight. The reaction mixture was partitioned between water and ethyl acetate. The organic phase was dried over anhydrous sodium sulfate and evaporated to give an amorphous (0.95 g). The amorphous was purified on a silica gel column, eluted with methylene chloride-ethyl acetate (19:1 and 9:1) to give the title compound (0.86 g) as white crystals.

EXAMPLE 9

Preparation of 3-(8-Chloro-6-fluoro-3,4-dihydro-2H-1,4-benzoxazin-5-yl)-1-methyl-6-trifluoromethyl-2,4(1H,3H)-pyrimidindione (Compound no. 2-1)

A mixture of 3-(2-amino-4-chloro-6-fluoro-3-hydroxyphenyl)-1-methyl-6-trifluoromethyl-2,4(1H,3H)-primidinedione (0.4 g), 1,2-dibromoethane (0.26 g) and potassium carbonate (0.312 g) in acetone (30 ml) was heated at reflux for 6 hours. The insoluble precipitate was removed through Celite and the filtrate was concentrated to an oil. The oily substance was purified by column chromatography on silica gel using ethyl acetate-hexane (1:2) as eluent to give the title compounds (0.028 g).

EXAMPLE 10

Preparation of 3-(4-Chloronaphthalen-1-yl)-1-methyl-6-trifluoromethyl-2,4(1H,3H)-pyrimidindione (Compound no. 5-1)

Step 1 Preparation of 4-Chloronaphthyl isocyanate as an Intermediate

To a solution of 4-chloronaphthyl amine(5 g) and triethylamine (5.65 g) in anhydrous ethyl acetate (100 ml) was added dropwise a solution of triphosgene (8.35 g) in anhydrous ethyl acetate (100 ml) at 0° C. After 15 minutes, the mixture was heated to reflux for 1 hour under a nitrogen atmosphere. The resulting mixture was allowed to cool to ambient temperature and filtered through Celite to remove the insoluble precipitate. The filtrate was concentrated to give the title compound as black solid.

Step 2 To a suspension of sodium hydride (1.23 g) in N,N-dimethylformamide (70 ml) was added dropwise a solution of ethyl 3-amino4,4,4-trifluorocrotonate (5.6 g) in toluene (50 ml) at 0° C. under nitrogen atmosphere. After 30 minutes, a solution of 4-chloronaphthyl isocyanate (28 mmol) in a mixed solvent of N,N-dimethylformamide (30 ml) and toluene (50 ml) was added dropwise at same temperature. The resulting solution was stirred for 2 hours at ambient temperature, and then methyl iodide (8 g) was added. After 12 hours, the reaction mixture was partitioned with water(200 ml) and a mixed solvent of ethyl acetate-hexane (1:1, 300 ml). The organic phase was washed with brine and dried over anhydrous sodium sulfate. The solvent was removed under reduced pressure and obtained solid was washed with hot ethyl acetate to give 3-(4-chloronaphthalen-1-yl)-1-methyl-6-trifluoromethyl-2,4(1H,3H)-pyrimidindione (6.6 g) as a brown solid.

EXAMPLE 11

Preparation of 2-(2-i-butyl-7-Chloro-5-fluorobenzoxazol-4-yl)-5-trifluoromethylpyridazin-3-one (Compound no. 12-2)

Step 1 Preparation of 2-(4-Chloro-6-fluoro-3-methoxy-2-nitrophenyl)-5-trifluoromethylpyridazin-3-one as an Intermediate 2-(4-Chloro-2-fluoro-5-methoxyphenyl)-5-trifluoromethylpyridazin-3-one was added to a mixture of conc. sulfuric acid (10 ml) and nitric acid (69%, 1 ml) with stirring at 0° C. After addition, the cold bath was removed and the resulting mixture was stirred for 0.5 hour at ambient temperature. Addition of the solution to ice-water resulted in yellow precipitate which was collected by filtration. The crude solid was purified by column chromatography on silica gel eluted with ethyl acetate and hexane (1:9) to give the title compound (0.53 g). $^1$H NMR (CDCl$_3$, 300 MHz) 4.05 (3H, s), 7.30 (1H, m), 7.53 (1H, d, J=8.7 Hz), 8.01 (1H, d, J=2.1 Hz) ppm.

Step 2 Preparation of 2-(2-Amino-4-chloro-6-fluoro-3-methoxyphenyl)-5-trifluoromethylpyridazin-3-one as an Intermediate A mixture of 2-(4-chloro-6-fluoro-3-methoxy-2-nitrophenyl)-5-trifluoromethylpyridazin-3-one (0.52 g) and iron powder (0.4 g) in acetic acid (30 ml) was stirred overnight at ambient temperature. The reaction solution was poured into water and extracted with ethyl acetate. The organic phase was washed with brine (×3) and dried over anhydrous sodium sulfate. The solvent was removed to give the title compound (0.46 g). $^1$H NMR (CDCl$_3$, 300 MHz) 3.88 (3H, s), 4.19 (2H, br s), 6.67 (1H, d, J=9.6 Hz), 7.31 (1H, m), 8.10 (1H, d, J=2.2 Hz) ppm.

Step 3 Preparation of 2-(2-Amino-4-chloro-6-fluoro-3-hydroxyphenyl)-5-trifluoromethylpyridazin-3-one as an Intermediate A mixture of 2-(2-amino-4-chloro-6-fluoro-3-methoxyphenyl)-5-trifluoromethylpyridazin-3-one (0.39 g) and borontribromide-methyl sulfide complex (1.8 g) in dichloroethane was heated at reflux temperature for 1 hour under nitrogen atmosphere. The mixture was poured into water and extracted with methylene dichloride. The organic phase was dried over anhydrous sodium sulfate and concentrated to give the title compound. $^1$H NMR (CDCl$_3$, 300 MHz) 4.61 (3H, br s), 6.55 (1H, d, J=9.4 Hz), 7.30 (1H, m), 8.05 (1H, d, J=2.2 Hz) ppm.

Step 4 Under nitrogen atmosphere 2-(2-amino-4-chloro-6-fluoro-3-hydroxyphenyl)-5-trifluoromethylpyridazin-3-one from step 3, trimethylacetyl chloride (0.17 g), triethylamine (0.14 g) and pyridinium p-toluenesulfonate in m-xylene(30 ml) was heated at reflux temperature overnight. The mixture was allowed to cool to ambient temperature and partitioned between ethyl acetate and brine. The organic phase was dried over anhydrous sodium sulfate and concentrated to an oil. The crude product was purified by column chromatography on silica gel eluted with ethyl. acetate-hexane (1:8) to afford 2-(2-t-butyl-7-chloro-5-fluorobenzoxazol-4-yl)-5-trifluoromethylpyridazin-3-one (0.26 g) as a pale yellow solid.

EXAMPLE 12

Preparation of 2-(2-t-butyl-7-Chloro-5-fluorobenzoxazol4-yl)-3-chloro-4,5,6,7-tetrahydropyrazolo[1,5-a]pyridine (Compound no 11-3)

Step 1 Preparation of 3-chloro-2-(4-chloro-6-fluoro-3-hydroxy-2-nitrophenyl)-4,5,6,7-tetrahydropyrazolo[1,5-a] pyridine as an intermediate 3-Chloro-2-(4-chloro-2-fluoro-5-hydroxyphenyl)-4,5,6,7-tetrahydropyrazolo[1,5-a] pyridine (1.0 g) was slowly added to stirred HNO$_3$ (69%, 6 ml) at 0° C. After 15 minutes, the resulting mixture was poured into ice water and resultant precipitate was separated by filtration to afford the title compound (1.1 g). $^1$H NMR (CDCl$_3$, 300 MHz) 1.95(2H, m), 2.10(2H, m), 2.80(2H, t, J=6.3 Hz), 4.17(2H, t, J=6.0 Hz), 6.0(1H, br s), 7.52(1H, d, J=8.2 Hz) ppm.

Step 2 Preparation of 3-chloro-2-(2-amino-4-chloro-6-fluoro-3-hydroxyhenyl)-4,5,6,7-tetrahydropyrazolo[1,5-a] pyridine 3-Chloro-2-(4-chloro-6-fluoro-3-hydroxy-2-nitrophenyl)-4,5,6,7-tetrahydropyrazolo[1,5-a]pyridine (1.1 g) was dissolved in glacial acetic acid (20 ml) and iron powder (0.55 g) was added. The suspension was stirred vigorously overnight at ambient temperature. The resulting solution was pertitioned between water and ethyl acetate. The organic phase was washed with saturated brine (×2), saturated sodium bicarbonate solution and dried over anhydrous sodium sulfate. The solvent was removed in vacuo to afford titled compound as an amorphous solid. 1H NMR (DMSO-d$_6$, 300 MHz 1.68(2H, m), 1.82(2H, m), 2.54(2H, t, J=6.1 Hz), 3.93(2H, t, J=5.7 Hz), 4.96(2H, brs), 6.37(1H, d, J=9.5 Hz), 8.82)1H, br s) ppm.

Step 3 3-Chloro-2-(2-amino-4-chloro-6-fluoro-3-hydroxyhenyl)-4,5,6,7-tetrahydropyrazolo[1,5-a]pyridine (0.3 g), triethylamine (0.12 g), pyridinium p-toluenesulfonate (0.14 g) and pivaloyl chloride (0.14 g) in m-xylene (20 ml) was refluxed overnight. Solvent was then evaporated under reduced pressure and the product was subjected to silica gel chromatography eluted with ethyl acetate and hexane (1:2). 2-(2-t-butyl-7-chloro-5-fluorobenzoxazol-4-yl)-3-chloro-4,5,6,7-tetrahydropyrazolo[1,5-a]pyridine was obtained (0.34 g).

EXAMPLE 13

Preparation of 4-Chloro-3-(8-chloro-6-fluoro-2-methyl-2H-1,4-benzoxazine-3-one-5-yl)-5-difluoromethoxy-1-methyl-i H-pyrazole (Compound no. 10-8)

Step 1 Preparation of 4-chloro-3-(4-chloro-6-fluoro-3-hydroxy-2-nitrophenol)-5-difluoromethoxy-1-methyl-1H-pyrazole as an Intermediate 4-Chloro-3-(4-chloro-2-fluoro-5-hydroxyphenyl)-5-difluoromethoxy-1-methyl-1H-pyrazole (2.8 g) was slowly added to HNO$_3$ (20 ml) at 0° C. The reaction mixture was stirred for 30 minutes at same temperature and poured into ice-water. Yellow precipitate was collected by filtration and washed with water (200 ml) to afford the title compound (2.95 g).

Step 2 Preparation of 4-Chloro-3-(2-amino-4-chloro-6-fluoro-3-hydroxyphenyl)-5-difluoromethoxy-1-methyl-1H-pyrazole as an Intermediate A mixture of 4-chloro-3-(4-chloro-6-fluoro-3-hydroxy-2-nitrophenol)-5-difluoromethoxy-1-methyl-1H-pyrazole (2.0 g) and iron powder (0.9 g) in acetic acid (50 ml) was stirred overnight at ambient temperature. The reaction solution was poured into water and extracted with ethyl acetate. The organic phase was washed with brine (×3) and dried over anhydrous sodium sulfate. The solvent was removed under reduced pressure to give the title compound (1.9 g) as a black oil.

Step 3 A mixture of 4-chloro-3-(2-amino-4-chloro-6-fluoro-3-hydroxyphenyl)-5-difluoromethoxy-1-methyl-1H-pyrazole (0.88 g), ethyl 2-bromopropionate (0.70 g) and potassiun carbonate (0.711 g) in acetonitrile (30 ml) was stirred overnight at ambient temperature. The reaction mixture was poured into water and extracted with ethyl acetate. The organic phase was washed with brine (×3) and dried over anhydrous sodium sulfate. The solvent was removed under reduced pressure and the oily product was subjected to silica gel chromatography eluted with ethyl acetate and hexane (1:4) to afford 4-chloro-3-(8-chloro-6-fluoro-2-methyl-2H-1,4-benzoxazine-3-one-5-yl)-5-difluoromethoxy-1-methyl-1H-pyrazole (0.054 g).

Using the procedures as described in Schemes 1–17 and Examples 1–12, the compounds of this invention can be readily prepared. Tables 1–17 list structures for few representative compounds of this invention.

The following abbreviations are used in the Tables below.

Me:methyl, Et:ethyl, Pr:propyl, Bu:butyl, Ph:phenyl, Ac:acetyl;

TABLE 1

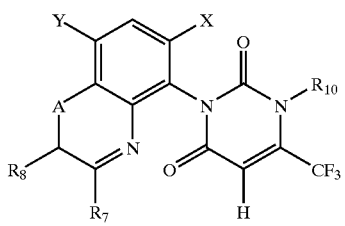

| Compd. No. | X | Y | A | R$_7$ | R$_8$ | R$_{10}$ |
|---|---|---|---|---|---|---|
| 1-1 | F | Cl | O | H | H | Me |
| 1-2 | F | Cl | O | Me | H | Me |
| 1-3 | F | Cl | O | Ph | H | Me |
| 1-4 | F | Cl | O | Me | H | NH2 |
| 1-5 | H | Cl | O | Me | Me | Me |
| 1-6 | F | Cl | O | Me | Me | Me |
| 1-7 | F | Cl | NH | Me | Me | Me |
| 1-8 | F | Cl | S | Me | Me | Me |
| 1-9 | F | CN | O | Me | H | Me |
| 1-10 | F | Cl | O | CO$_2$Me | H | Me |
| 1-11 | F | Cl | O | cyclopropyl | H | Me |

TABLE 2

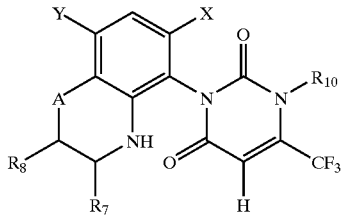

| Compd. No. | X | Y | A | R$_7$ | R$_8$ | R$_{10}$ |
|---|---|---|---|---|---|---|
| 2-1 | F | Cl | O | H | H | Me |
| 2-2 | F | Cl | S | H | H | Me |
| 2-3 | F | Cl | O | H | H | NH2 |
| 2-4 | F | Cl | NH | H | H | Me |
| 2-5 | F | Cl | O | Me | H | Me |
| 2-6 | F | Cl | O | Me | Me | Me |
| 2-7 | F | CN | O | H | H | Me |
| 2-8 | F | Cl | O | H | —CH(Me)CO$_2$Me | Me |
| 2-9 | F | Cl | O | H | —CH$_2$CH(Cl)CO$_2$Et | Me |

TABLE 3

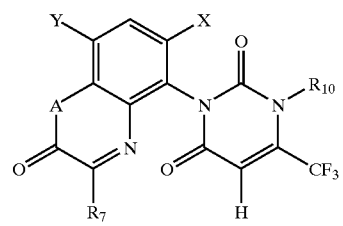

| Compd. No. | X | Y | A | R$_7$ | R$_{10}$ |
|---|---|---|---|---|---|
| 3-1 | F | Cl | O | Me | Me |
| 3-2 | F | Cl | NH | Me | Me |
| 3-3 | F | Cl | S | Me | Me |
| 3-4 | F | Cl | O | Ph | Me |
| 3-5 | F | Cl | O | CO$_2$Et | Me |
| 3-6 | F | Cl | O | Me | NH$_2$ |

TABLE 4

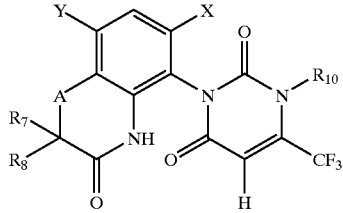

| Compd. No. | X | Y | A | R$_7$ | R$_8$ | R$_{10}$ |
|---|---|---|---|---|---|---|
| 4-1 | F | Cl | O | H | H | Me |
| 4-2 | F | Cl | O | H | H | NH$_2$ |
| 4-3 | F | Cl | O | Me | H | Me |
| 4-4 | F | Cl | S | H | H | Me |
| 4-5 | F | Cl | NH | H | H | Me |
| 4-6 | F | Cl | CH$_2$ | H | H | Me |
| 4-7 | F | Cl | O | CO$_2$Me | H | Me |
| 4-8 | F | Cl | O | cyclopropyl | H | Me |
| 4-9 | F | Cl | O | Ph | H | Me |
| 4-10 | F | Cl | O | Me | Me | Me |
| 4-11 | F | Cl | O | —CH$_2$CH(Cl)CO$_2$Et | H | Me |
| 4-12 | F | Cl | O | —CH$_2$CH(Cl)CO$_2$Et | Me | Me |
| 4-13 | F | Cl | O | Cl | H | Me |
| 4-14 | Cl | Cl | O | Me | Me | Me |

TABLE 5

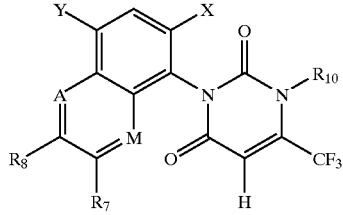

| Compd. No. | X | Y | A | M | R$_7$ | R$_8$ | R$_{10}$ |
|---|---|---|---|---|---|---|---|
| 5-1 | H | Cl | CH | CH | H | H | Me |
| 5-2 | F | Cl | CH | CH | H | H | Me |

TABLE 5-continued

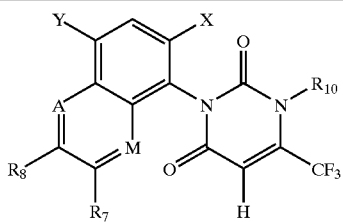

| Compd. No. | X | Y | A | M | $R_7$ | $R_8$ | $R_{10}$ |
|---|---|---|---|---|---|---|---|
| 5-3 | F | Cl | CH | CH | Me | H | Me |
| 5-4 | F | Cl | CH | N | H | H | Me |
| 5-5 | F | Cl | N | CH | H | H | Me |
| 5-6 | F | Cl | CH | CH | Me | Me | Me |
| 5-7 | F | Cl | N | N | H | H | Me |
| 5-8 | F | Cl | CH | CH | H | $CO_2Me$ | Me |
| 5-9 | F | Cl | CH | CH | ▷ | H | Me |
| 5-10 | F | Cl | $CNO_2$ | CH | H | H | Me |
| 5-11 | F | Cl | CH | CH | H | H | $NH_2$ |

TABLE 6

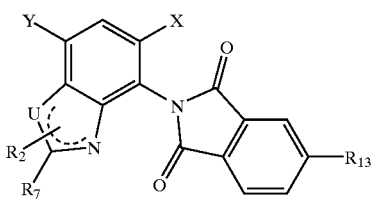

| Compd. No. | X | Y | U | $R_2$ | $R_7$ | $R_{13}$ |
|---|---|---|---|---|---|---|
| 6-1 | F | Cl | O | — | Me | H |
| 6-2 | F | Cl | O | — | t-Bu | H |
| 6-3 | F | Cl | S | — | t-Bu | H |
| 6-4 | F | Cl | O | — | t-Bu | F |
| 6-5 | F | Cl | N | H | t-Bu | H |

TABLE 7

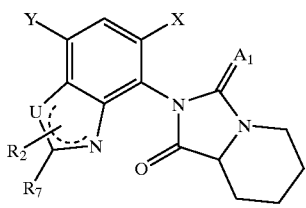

| Compd. No. | X | Y | U | $R_2$ | $R_7$ | $A_1$ |
|---|---|---|---|---|---|---|
| 7-1 | F | Cl | N | H | Me | S |
| 7-2 | F | Cl | N | H | Et | S |
| 7-3 | F | Cl | N | H | t-Bu | S |
| 7-4 | F | Cl | O | — | Me | S |
| 7-5 rotamer 2 | F | Cl | O | — | Et | S |
| 7-6 rotamer 1 | F | Cl | O | — | Et | S |
| 7-7 | F | Cl | O | — | t-Bu | S |
| 7-8 | F | Cl | O | — | Me | O |
| 7-9 | F | Cl | O | — | Et | O |

TABLE 7-continued

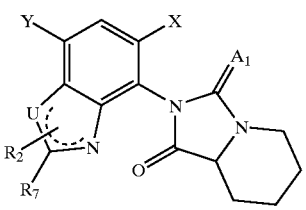

| Compd. No. | X | Y | U | $R_2$ | $R_7$ | $A_1$ |
|---|---|---|---|---|---|---|
| 7-10 | F | Cl | N | H | t-Bu | O |
| 7-11 | F | Cl | N | H | t-Bu | O |

TABLE 8

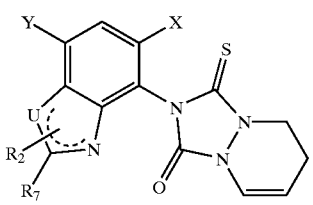

| Compd. No. | X | Y | U | $R_2$ | $R_7$ |
|---|---|---|---|---|---|
| 8-1 | F | Cl | O | — | Et |
| 8-2 | F | Cl | O | — | t-Bu |
| 8-3 | F | Cl | S | — | t-Bu |
| 8-4 | F | Cl | N | H | t-Bu |
| 8-5 | F | Cl | N | Me | t-Bu |

TABLE 9

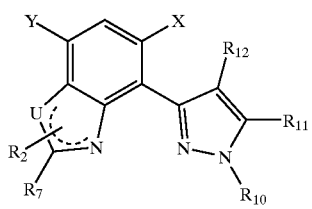

| Compd. No. | X | Y | U | $R_2$ | $R_7$ | $R_{10}$ | $R_{11}$ | $R_{12}$ |
|---|---|---|---|---|---|---|---|---|
| 9-1 | F | Cl | N | H | Et | Me | $CF_3$ | Cl |
| 9-2 | Cl | Cl | N | H | Et | Me | $CF_3$ | Cl |
| 9-3 | F | Cl | N | H | t-Bu | Me | $CF_3$ | Cl |
| 9-4 | F | Cl | N | H | t-Bu | Me | $CF_3$ | Br |
| 9-5 | H | Cl | N | H | t-Bu | Me | $CF_3$ | Cl |
| 9-6 | Cl | Cl | N | H | t-Bu | Me | $CF_3$ | Cl |
| 9-7 | F | Cl | N | H | t-Bu | Me | $OCHF_2$ | Cl |
| 9-8 | F | Cl | N | Me | t-Bu | Me | $CF_3$ | Cl |
| 9-10 | F | Cl | N | H | $CH_2CO_2Me$ | Me | $CF_3$ | |

TABLE 10

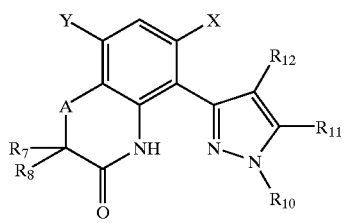

| Compd. No. | X | Y | A | $R_7$ | $R_8$ | $R_{10}$ | $R_{11}$ | $R_{12}$ |
|---|---|---|---|---|---|---|---|---|
| 10-1 | F | Cl | O | H | H | Me | $CF_3$ | Cl |
| 10-2 | F | Cl | O | Me | H | Me | $CF_3$ | Cl |
| 10-3 | F | Cl | O | Me | Me | Me | $CF_3$ | Cl |
| 10-4 | Cl | Cl | O | H | H | Me | $CF_3$ | Cl |
| 10-5 | F | Br | O | Me | Me | Me | $CF_3$ | Cl |
| 10-6 | F | Cl | O | Me | Me | Me | $CF_3$ | Br |
| 10-7 | H | Cl | O | Me | Me | Me | $CF_3$ | Cl |
| 10-8 | F | Cl | O | Me | H | Me | $OCHF_2$ | Cl |
| 10-9 | F | Cl | O | Me | Me | Me | $OCHF_2$ | Cl |
| 10-10 | F | Cl | O | Me | Me | Me | $OCHF_2$ | Br |
| 10-11 | H | Cl | O | Me | H | Me | $OCHF_2$ | Cl |
| 10-12 | F | F | O | Me | Me | Me | $OCHF_2$ | Cl |
| 10-13 | F | Cl | NH | H | H | Me | $OCHF_2$ | Cl |
| 10-14 | F | Cl | O | H | H | Me | $OCHF_2$ | Cl |
| 10-15 | F | Cl | S | H | H | Me | $CF_3$ | Cl |
| 10-16 | F | Cl | S | Me | H | Me | $OCHF_2$ | Cl |
| 10-17 | F | Cl | O | Me | Me | Me | $OCHF_2$ | CN |

TABLE 11

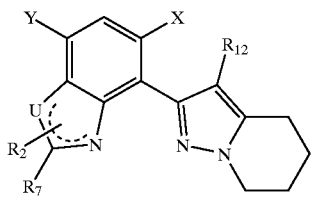

| Compd. No. | X | Y | U | $R_2$ | $R_7$ | $R_{12}$ |
|---|---|---|---|---|---|---|
| 11-1 | H | Cl | O | — | t-Bu | Cl |
| 11-2 | Cl | Cl | O | — | t-Bu | Cl |
| 11-3 | F | Cl | O | — | t-Bu | Cl |
| 11-4 | F | Cl | N | H | Me | Cl |
| 11-5 | F | Cl | O | — | t-Bu | Br |
| 11-6 | F | Cl | O | — | t-Bu | CN |
| 11-7 | F | Cl | O | — | Me | Cl |
| 11-8 | H | Cl | S | — | t-Bu | Cl |
| 11-9 | F | Cl | O | — | t-Bu | —≡—H |

TABLE 12

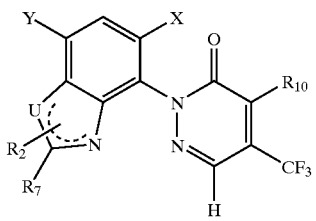

| Compd. No. | X | Y | U | $R_2$ | $R_7$ | $R_{10}$ |
|---|---|---|---|---|---|---|
| 12-1 | F | Cl | O | — | Me | H |
| 12-2 | F | Cl | O | — | t-Bu | H |
| 12-3 | F | Cl | O | — | t-Bu | Me |
| 12-4 | F | Cl | S | — | t-Bu | Me |
| 12-5 | F | Cl | N | H | t-Bu | Me |
| 12-6 | F | Cl | N | Me | t-Bu | Me |

TABLE 13

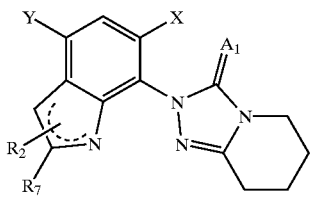

| Compd. No. | X | Y | U | $R_2$ | $R_7$ | $A_1$ |
|---|---|---|---|---|---|---|
| 13-1 | H | Cl | O | — | Me | O |
| 13-2 | H | Cl | O | — | t-Bu | O |
| 13-3 | F | Cl | O | — | t-Bu | O |
| 13-4 | Cl | Cl | O | — | t-Bu | O |
| 13-6 | F | F | O | — | t-Bu | O |
| 13-7 | F | Cl | N | H | t-Bu | O |
| 13-8 | F | Cl | O | — | t-Bu | S |
| 13-9 | F | Cl | S | — | t-Bu | O |
| 13-10 | F | Cl | S | — | Me | O |

TABLE 14

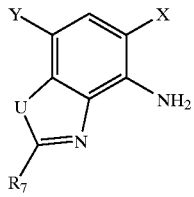

| Compd. No. | X | Y | U | $R_7$ |
|---|---|---|---|---|
| 14-1 | F | Cl | O | H |
| 14-2 | F | Cl | O | Me |
| 14-3 | F | Cl | O | Et |
| 14-4 | F | Cl | O | t-Bu |
| 14-5 | F | Cl | O | 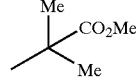 |

TABLE 14-continued

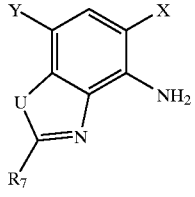

| Compd. No. | X | Y | U | R7 |
|---|---|---|---|---|
| 14-6 | F | Cl | O | 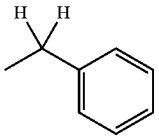 |
| 14-7 | F | Cl | O | 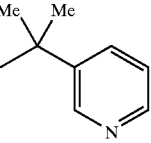 |
| 14-8 | F | Cl | O | 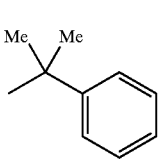 |
| 14-9 | H | Cl | O | t-Bu |
| 14-10 | Cl | Cl | O | t-Bu |
| 14-11 | F | Cl | S | Me |
| 14-12 | F | CN | O | Me |
| 14-13 | F | CN | O | t-Bu |
| 14-14 | F | CF3 | O | t-Bu |
| 14-15 | F | Cl | NH | t-Bu |
| 14-16 | F | OCHF2 | O | Et |
| 14-17 | F | NO2 | O | t-Bu |
| 14-18 | F | Br | O | t-Bu |
| 14-19 | F | F | O | t-Bu |

TABLE 15

| Compd. No. | $^1$H-NMR(300MHz, ppm) |
|---|---|
| 1-3 | 3.57(3H, s), 5.15(1H, d, J=15.3Hz), 5.20(1H, d, J=15.3Hz), 6.40(1H, s), 7.15(1H, d, J=9.0Hz), 7.4–7.8(5H, m). |
| 2-1 | 3.57(3H, d, J=1.1Hz), 3.71(2H, dd, J=5.4, 4.2Hz), 4.28(1H, br s), 4.38(2H, dd, J=5.4, 4.2Hz), 6.37(1H, s), 6.65(1H, d, J=9.3Hz). |
| 3-1 | 2.55(3H, s), 3.58(3H,br d, J=1.1Hz), 6.39(1H, s), 7.49(1H, d, J=8.7Hz). |
| 4-1 | 3.45(3H, s), 4.75(2H, s), 6.59(1H, s), 7.27(1H, d, J=9.4Hz), 11.13(1H, s). |
| 4-2 | 4.70(2H, s), 5.55(2H, s), 6.28(1H, s), 7.14(1H, d, J=9.3Hz), 11.2(1H, s). |
| 4-3 | 1.45(1.5H, d, J=6.8Hz), 1.47(1.5H d, J=6.8Hz), 3.44(3H, s), 4.84(0.5H, q, J=6.8Hz), 4.86 (0.5H, q, J=6.8Hz), 6.60(1H, s), 7.29(1H, d, J=9.4Hz), 11.10(0.5H, s), 11.2(0.5H, s). |
| 4-10 | 1.41(3H, s), 1.45(3H, s), 3.43(3H, s), 6.65(1H, s), 7.36(1H, d, J=9.5Hz). |
| 5-1 | 3.59(3H, br d J=1.3Hz), 6.45(1H, s), 7.31(1H, d, J=7.9Hz), 7.5–7.7(4H, m), 8.36(1H, dd, J=7.6, 0.5Hz). |
| 6-2 | 1.47(9H, s), 7.60(1H, d, J=10.2Hz), 7.90–8.10(4H, m). |
| 7-5 | 1.43(3H, t, J=7.6Hz), 1.63(3H, m), 1.9(1H, m), 2.1(1H, m), 2.4(1H, m), 2.99(2H, q, J=7.6Hz), 4.17(1H, m), 4.90(1H, m), 7.25(1H, d, J=9.6Hz). |
| 7-6 | 1.43(3H, t, J=7.6Hz), 1.7(3H, m), 1.9(1H, m), 2.1(1H, m), 2.37(1H, m), 2.97(2H, q, 3=7.6Hz), 3.13(1H, m), 4.13(1H, m), 4.89(1H, m), 7.24(1H,d, J=9.7Hz). |
| 7-9 | 1.43(3H, t, J=7.6), 1.57(3H, m), 1.79(1H, m), 2.08(1H, m), 2.34(1H, m), 2.99(2H, 2q), 4.05(1H, m), 4.26(1H, m), 7.25(1H, 2d). |
| 8-1 | 1.44(3H, t, 3=7.4Hz), 2.60(2H, m), 3.02(2H, q, J=7.6Hz), 4.32(2H, m), 5.40(1H, m), 6.89(1H, d, J=8.2Hz), 7.30(1H, d, J=9.8Hz). |
| 10-8 | 1.62(3H, d, J=6.8Hz), 3.87(3H, s), 4.70(1H, q, J=6.8Hz), 6.74(1H, t, J=72.0Hz), 6.92(1H, d, J=9.3Hz), 8.91(1H, br s). |
| 10-9 | 1.56(6H, s), 3.88(3H, s), 6.74(1H, t, J=72.0Hz), 6.92(1H, d, J=9.4Hz), 8.82(1H, Br s). |
| 11-3 | 1.49(9H, s), 1.94(2H, m), 2.08(2H, m), 2.79(2H, t, J=6.3Hz), 4.22(2H, t, J=5.9Hz), 7.18(1H, d, J=10.0 Hz). |
| 14-3 | 1.45(3H, t, J=7.6Hz), 2.96(2H, q, J=7.5Hz), 4.28(2H, br s), 7.01(1H, d, J=11.2Hz). |
| 14-18 | 1.48(9H, s), 4.25(2H, br s), 7.12(1H, d, J=1.0Hz). |

HERBICIDAL ACTIVITY

The compounds of the present invention exhibit excellent herbicidal effects when used as an active ingredient of a herbicide. The herbicide can be used for a wide range of applications, for example on crop lands such as paddy fields, upland farms, orchards, vinyards and mulberry fields, and non-crop lands such as forests, turf, rights of way, roadsides, railways, farm roads, playgrounds, and factory sites. The application method may be suitably selected for soil treatment application and foliar application.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), goosegrass (*Eleusine indica L.*), wild oat (*Avena fatua L.*), Johnsongrass (*Sorghum halepense*), quackgrass (*Agropyron repens*), alexandergass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria L.*), purple nutsedge (*Cyperus rotundus L.*), Japanese bulrush (*Scirpus Juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and nartowleaf waterplantain (*Alisma canaliculatum*); ponteteriaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lythraceae such as toothcup (*Rotala indica*) and red stem (*Ammannia multiflora*); and broadleaves such as redroot pigweed (*Amaranthus retroflexus*), velvetleaf (*Abutilon theophrasti*), morningglory (*Ipomoea hedeiracea*), lambsquarters (*Chenopodium album*), prickly sida (*Sida spinosa L.*), common pursiane (*Portulaca oleracea L.*), slender amaranth (*Amaranthus viridis L.*), sicklepod (*Cassia obtusifolia*), black nightshade (*Solanum nigrum L.*), pale smartweed (*Polygonum lapathifolium L.*), common chickweed (*Stellaria media L.*), common cocklebur (*Xanthium strumarium L.*), flexuous bittercress (*Cardamine flexuosa* WITH.), henbit (*Lamium amplexicaule L.*) and threeseeded copperleaf (*Acalypha australis L.*). Accordingly, it is useful for controlling noxious weeds non-selectively or selectively in the cultivation of a crop plant such as corn (*Zea maps L.*), soybean (*Glycine niax*

*Merr.*), cotton (*Gossypiurn* spp.), wheat (*Triticum* spp.), rice (*Oryza sativa* L.), barley (*Hordeum vulgare* L.), oat (*Avena sativa* L.), sorghum (*Sorghum bicolor* Moench), canola (*Brassica napus* L.), sunflower (*Helianthus annuus* L.), sugar beet (*Beta vulgaris* L.), sugar cane (*Saccharum officinarum* L.), Japanese lawngrass (*Zoysia Japonica stend*), peanut (*Arachis hypogaea* L.) or flax (*Linum usitatissimum* L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder.(said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, with additional solvents. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as a emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

The compositions of the present invention may be used in admixture with or in combination with other agricultural chemicals, fertilizers, adjuvants, surfactants, emulsifiers, oils, polymers or phytotoxicity-reducing agents such as herbicide safeners. In such a case, they may exhibit even better effects or activities. As other agricultural chemicals, herbicides, fungicides, antibiotics, plant hormones, plant growth regulators, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha. The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

1. Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2,3,6 TBA, dicamba, dichlobenil, a pyridine type such as picloram (including free acids and salts thereof), triclopyr or clopyralid and others such as naptalam, benazolin, quinclorac, quinmerac or diflufenzopyr (BAS 654H).
2. Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, terbuthylazine, atraton, hexazinone, metribuzin, simetryn, ametryn, prometryn, dimethametryn or triaziflam, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon and methazole.
3. A quaternary ammonium salt type such as paraquat, diquat or difenzoquat, which is believed to form active oxygen in the plant and thus to exhibit quick herbicidal effects.
4. Those which are believed to exhibit herbicidal effects by inhibiting chlorophyll biosynthesis in plants and abnormally accumulating a photosensitizing peroxide substance in the plant body, including a diphenyl ether type such as nitrofen, lactofen, acifluorfen-sodium, oxyfluorfen, fomesafen, bifenox, or chlomethoxyfen, a cyclic imide type such as chlorphthalim, flumioxazin, cinidon-ethyl, or flumiclorac-pentyl, and others such as oxadiazon, sulfentrazone, thidiazimin, azafenidin, carfentrazone, isopropazole, fluthiacet-methyl, pentoxazone, pyraflufen-ethyl and oxadiargyl.
5. Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, diflufencam, methoxyphenone, clomazone, amitrole, sulcotrione, mesotrione, isoxaflutole and isoxachlortole.
6. Those which exhibit herbicidal effects specifically to gramineous plants including an aryloxyphenoxypropionic acid type (either as a mixture of isomers or as a resolved isomer) such as diclofop-methyl, pyrofenop-sodium, fluazifop butyl or fluazifop-p-butyl, haloxyfop-methyl, quizalofop p-ethyl, quizalafop p-tefiiryl, fenoxaprop ethyl or fenoxaprop-p-ethyl, flamprop-M-methyl or flamprop-m-isopropyl or cyhalofop-butyl and a cyclohexanedione type such as alloxydim-sodium, sethoxydim, clethodim, tepraloxydim or tralkoxydim.
7. Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron or halosulfuron-methyl, thifensulfuron-methyl, rimsulfuron, azimsulfuron, flazasulfuron, imazosulfuron, cyclosulfamuron, flupyrsulfuron, iodosulfuron, ethoxysulfuron, flucarbazone, sulfosulfuron, oxasulfuron a triazolopyrimidinesulfonamide type such as flumetsulam, metosulam, chloransulam or chloransulam-methyl, an imidazolinone type such as imazapyr, imazethapyr, imazaquin, imazamox, imazameth, imazamethabenz methyl, a pyrimidinesalicylic acid type such as pyrthiobac-sodium, bispyribac-sodium, pyriminobac-methyl or pyribenzoxim (LGC-40863), and others such as glyphosate, glyphosate-ammonium, glyphosate-isopropylamine or sulfosate.
8. Those which are believed to exhibit herbicidal effects by interfering with the normal metabolism of inorganic nitrogen assimilation such as glufosinate, glufosinate-ammonium, phosphinothricin or bialophos.
9. Those which are believed to exhibit herbicidal effects by inhibiting cell division of plant cells, including a dinitroaniline type such as trifluralin, oryzalin, nitralin, pendamethalin, ethafluralin, benefin and prodiamine, an amidetype such as bensulide, napronamide, and pronamide, a carbamate type such as propham, chlorpropham, barban, and asulam, an organophosphorous type such as amiprofos-methyl or butamifos and others such as DCPA and dithiopyr.
10. Those which are believed to exhibit herbicidal effects by inhibiting protein synthesis of plant cells, including a chloroacetanilide type such as alachlor, metolachor (including combinations with safeners such as benoxacor, or resolved isomeric mixtures of metolachlor including safeners such as benoxacor) propachlor, acetochlor (including combinations with herbicide safeners such as dichlornid or MON 4660 or resolved isomeric mixtures of acetochlor containing safeners such as dichlormid or MON 4660), propisochlor or dimethenamid or an oxyacetamide type such as flufenacet.

11. Those in which the mode of action causing the herbicidal effects are not well understood including the dithiocarbamates such as thiobencarb, EPTC, diallate, triallate, molinate, pebulate, cycloate, butylate, vemolate or prosulfocarb and miscellaneous herbicides such as MSMA, DSMA, endothall, ethofumesate sodium chlorate, pelargonic acid and fosamine.

A few fonnulation examples of the present invention are given as follows.

Formulation example 1. Emulsifiable Concentrate

| Ingredient Trade Name | Chemical Name | Supplier | Function | % wt./wt. |
|---|---|---|---|---|
| Compound 4-3 | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |

Formulation example 2. Suspension Concentrate

| Ingredient Trade Name | Chemical Name | Supplier | Function | % wt./wt. |
|---|---|---|---|---|
| Compound 2-1 | | | Active Ingredient | 10.00 |
| Proylene gylcol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D-425 | Napthalene formaldehyde condensate | Witco Corp. | Dispersant | 3.00 |
| Igepal CA-720 | Octylphenol ethoxylate | Rhone-Poulenc | Wetting agent | 3.00 |
| Proxel GXL | 1,2 benzisothiazoln-3-one | ICI Americas | Preservative | 0.25 |
| Water | | | Diluent | 68.00 |

Formulation example 3. Wettable Powder

| Ingredient Trade Name | Chemical Name | Supplier | Function | % wt./wt. |
|---|---|---|---|---|
| Compound 8-1 | | | Active Ingredient | 50.00 |
| Geropon T-77 | Sodium-N-methyl-N | Rhone-Poulenc | Wetting agent | 3.00 |
| Lomar PW | oleoyl taurate Napthalene Sulfonate | Henkel Corp. | Dispersant | 5.00 |
| Kaolin clay | Kaolin clay | J. M. Huber | Filler | 42.00 |

Formulation example 4. Water Dispersible Granule

| Ingredient Trade Name | Chemical Name | Supplier | Function | % wt./wt. |
|---|---|---|---|---|
| Compound 10-8 | | | Active Ingredient | 50.00 |
| Morwet EFW | | Witco Corp. | Wetting agent | 2.00 |
| Morwet D-425 | Napthalene formaldehyde condensate | Witco Corp. | Dispersant | 10.00 |
| ASP 400 | Kaolin Clay | Engelhard Corp. | Filler | 38.00 |

Test Example

A standard greenhouse herbicide activity screening system was used to evaluate the herbicidal efficacy and crop safety of these test compounds. Seven broadleaf weed species including redroot pigweed (*Amaranthus retroflexus*, AMARE), velvetleaf (*Abutilon theophrasti*, ABUTH), sicklepod (*Cassia obtusifolia*, CASOB), ivyleaf morningglory (*Ipomoea hederacea*, IPOHE), lambsquarters (*Chenopodium album*, CHEAL), common ragweed (*Ambrosia artemisiifolia L.*, AMBEL), and cocklebur (*Xanthium strumarium*, XANST) were used as test species. Four grass weed species including green foxtail (*Setaria viridis*, SETVI), barnyardgrass (*Echinochloa crus-galli*, ECHCG), johnsongrass (*Sorghum halepense*, SORHA), and large crabgrass (*Digitaria sanguinalis*, DIGSA) were also used. In addition, three crop species, field corn (*Zea mays L.*, var. Dekalb 527, CORN), soybean (*Glycine max L.*, var. Pella 86, SOY), and upland rice (Ory0a sp., var.Tebonnet, RICE) were included.

Pre-emerge Test

All plants were grown in 10 cm square plastic pots which were filled with a sandy loam soil mix. For pre-emerge tests, seeds were planted one day prior to application of the test compounds. For post-emerge tests, seeds were planted 8–21 days prior to the test to allow emergence and good foliage development prior to application of the test substances. At the time of the post-emerge application, plants of all species were usually at the 2–3 leaf stage of development.

All test compounds were dissolved in acetone and applied to the test units in a volume of 187 l/ha. Test materials were applied at rates ranging from 15 g ai/ha to 1000 g ai/ha using a track sprayer equipped with a TJ8001E even flow flat fan spray nozzle. Plants were arranged on a shelf so that the top of the canopy (post-emerge) or top of the soil surface (pre-emerge) was 40–45 cm below the nozzle. Pressurized air was used to force the test solution through the nozzle as it was mechanically advanced over the top of all test plants/pots. This application simulates a typical commercial field herbicide application.

Post-emerge Test

In the post-emerge test, a commercial non-ionic surfactant was also included (0.25% v/v) to enhance wetting of the leaf surfaces of target plants. Immediately after application, test units of the pre-emerge applications were watered at the soil surface to incorporate the test materials.

At 14 days after application of the test materials, phytotoxicity ratings were recorded. A rating scale of 0-100 was used as previously described in *Research Methods in Weed Science*, 2nd edition, B. Truelove, Ed., Southern Weed Science Society, Auburn University, Auburn, Ala., 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound No. in Tables 1–14, are shown in Tables 16 and 17. The data demonstrate significant differences between compounds for both efficacy against weeds and selectivity for crop species. For selected compounds, excellent activity against a majority of the weed species was observed with minimal damage to at least one of the crop species.

Tables 16 and 17 show pre-emerge and post-emerge herbicidal activity data respectively for a few representative examples of the compounds described herein.

What is claimed is:

1. A compound of the formula or its salt represented by the formula (Ia)

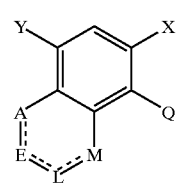

in which

X and Y are independent of each other and are represented by halogen, cyano, nitro, $(C_{1-4})$alkyl, $(C_{1-4})$alkoxy, $(C_{1-4})$haloalkyl or $(C_{1-4})$haloalkoxy;

A is oxygen or sulfur

M is nitrogen or $NR_2$,

E and L are independent of each other and may be selected from $CR_7$, $CR_8$, $CR_7R_8$, $C(=O)$, $C(=S)$, $C(=NR_7)$ or $CNR_7R_8$;

$R_2$ is selected from the group consisting of hydrogen, $(C_{1-6})$alkyl, $(C_{2-6})$alkenyl, $(C_{2-6})$alkynyl, $(C_{1-6})$alkylcarbonyl, $(C_{1-6})$cycloalkylcarbonyl, $(C_{1-6})$haloalkylcarbonyl, $(C_{1-6})$alkoxycarbonyl, arylcarbonyl

TABLE 16

Pre-emerge Herbicidal Activity

| Compd. No. | Rate g ai/ha | AM ARE | ABU TH | CAS OB | IPO HE | CHE AL | AMB EL | SET VI | ECH CG | SOR HA | DIG SA | SOY | COR N | RICE |
|---|---|---|---|---|---|---|---|---|---|---|---|---|---|---|
| 1-3 | 250 | 100 | 80 | 80 | 0 | 100 | — | 80 | 0 | 0 | 0 | 0 | 0 | 10 |
| 2-1 | 125 | 100 | 100 | 40 | 50 | 100 | — | 100 | 50 | 95 | 100 | 50 | 20 | 70 |
| 2-8 | 250 | 100 | 100 | 100 | 100 | 100 | — | 100 | 60 | 100 | 100 | 100 | 70 | 50 |
| 3-1 | 250 | 60 | 100 | 0 | 0 | 100 | — | 20 | 0 | 0 | 0 | 0 | 0 | 0 |
| 3-5 | 250 | 50 | 65 | 0 | 0 | 70 | — | 0 | 0 | 0 | 0 | 0 | 0 | 0 |
| 4-1 | 250 | 100 | 100 | 100 | 100 | 100 | — | 100 | 70 | 95 | 100 | 100 | 90 | 90 |
| 4-2 | 250 | 100 | 100 | 100 | 100 | 100 | — | 80 | 80 | 65 | 70 | 95 | 100 | 90 |
| 4-3 | 250 | 100 | 100 | 100 | 100 | 100 | — | 100 | 99 | 100 | 100 | 100 | 99 | 99 |
| 5-1 | 500 | 100 | 100 | 60 | 60 | 100 | — | 100 | 60 | — | 98 | 70 | 70 | 70 |
| 7-5 | 250 | 50 | 30 | 0 | 0 | 60 | — | 0 | 0 | — | 0 | 0 | 0 | 0 |
| 7-9 | 250 | 100 | 50 | 10 | 20 | 100 | — | 40 | 10 | — | 30 | 15 | 0 | 10 |
| 8-1 | 250 | 100 | 100 | 90 | 60 | 100 | — | 100 | 90 | 100 | 100 | 60 | 50 | 20 |
| 10-8 | 250 | 100 | 100 | 95 | 99 | 100 | — | 100 | 100 | 99 | 100 | 15 | 0 | 40 |
| 12-1 | 250 | 100 | 100 | 90 | 99 | 100 | — | 100 | 100 | 100 | 100 | 70 | 100 | 90 |

TABLE 17

Post-emerge Herbicidal Activity

| Compd. No. | Rate g ai/ha | AM ARE | ABU TH | CAS OB | IPO HE | CHE AL | AMB EL | SET VI | ECH CG | SOR HA | DIG SA | SOY | COR N | RICE |
|---|---|---|---|---|---|---|---|---|---|---|---|---|---|---|
| 1-3 | 250 | 60 | 90 | 0 | 30 | 20 | — | 0 | 0 | 0 | 0 | 30 | 10 | 20 |
| 2-1 | 125 | 90 | 100 | 80 | 100 | 100 | — | 50 | 10 | 0 | 0 | 90 | 20 | 40 |
| 2-8 | 250 | 100 | 100 | 50 | 100 | 100 | 100 | 100 | 80 | 95 | 50 | 100 | 70 | 90 |
| 3-1 | 250 | 70 | 95 | 0 | 50 | 60 | 20 | 0 | 0 | 0 | 0 | 30 | 0 | 0 |
| 3-5 | 250 | 20 | 60 | 0 | 0 | 0 | — | 10 | 0 | 0 | 0 | 0 | 0 | 0 |
| 4-1 | 250 | 100 | 100 | 80 | 100 | 100 | — | 10 | 30 | 40 | 30 | 100 | 70 | 65 |
| 4-2 | 250 | 100 | 100 | 90 | 100 | 100 | — | 40 | 60 | — | 20 | 100 | 90 | 90 |
| 4-3 | 250 | 100 | 100 | 95 | 100 | 100 | — | 50 | 80 | 90 | 70 | 100 | 100 | 80 |
| 5-1 | 500 | 100 | 100 | 60 | 60 | 100 | — | 100 | 70 | — | 60 | 0 | 0 | 0 |
| 7-5 | 250 | 100 | 100 | 100 | 100 | 100 | — | 60 | 0 | 0 | 10 | 80 | 20 | 10 |
| 7-6 | 250 | 30 | 90 | 30 | 70 | 60 | — | 10 | 0 | — | 0 | 50 | 30 | 10 |
| 8-1 | 250 | 100 | 100 | 100 | 100 | 99 | — | 100 | 90 | 99 | 70 | 100 | 80 | 80 |
| 10-8 | 250 | 100 | 100 | 100 | 100 | 100 | 95 | 100 | 100 | 55 | 65 | 100 | 25 | 90 |
| 12-1 | 250 | 70 | 95 | 10 | 40 | 0 | 20 | 0 | 50 | 0 | 0 | 50 | 0 | 10 | and heteroarylcarbonyl; where any of these groups may be optionally substituted with one or more of the following groups consisting of halogen, hydroxy, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;

$R_7$ and $R_8$ are independent of each other and may be selected from the group consisting of hydrogen, halogen, hydroxy, mercapto, amino, cyano, nitro, $(C_{1-6})$alkyl, $(C_{1-6})$haloalkyl, $(C_{1-6})$alkoxy, $(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl, $(C_{1-6})$alkylamino, arylsulfonylamino, arylamino, $(C_{1-6})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxy, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, haloaryl, alkoxyaryl, aryoxy, arylthio, haloaryloxy, heteroaryl, heteroaryloxy and $(C_{3-7})$cycloalkyl;

Q is selected from;

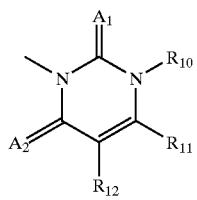

Q₁

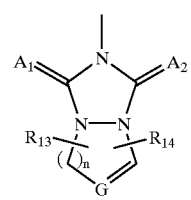

Q₂

-continued

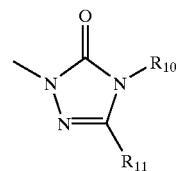

Q₃

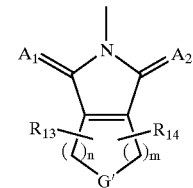

Q₄

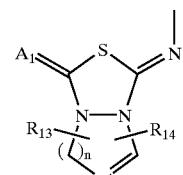

Q₅

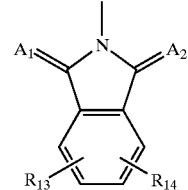

Q₆

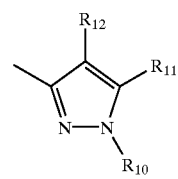

Q₇

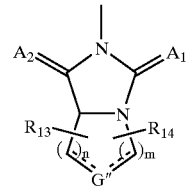

Q₈

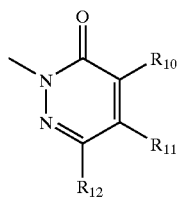

Q₉

Q10 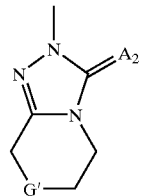

Q11 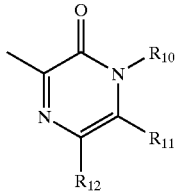

Q12 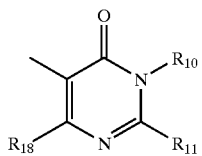

Q13 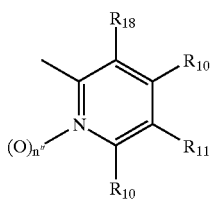

Q14 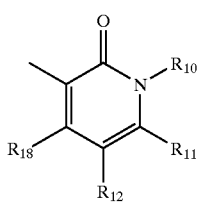

Q15 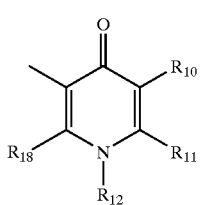

Q16 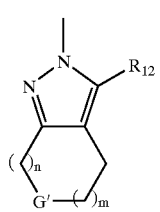

Q17 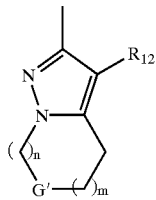

Q18 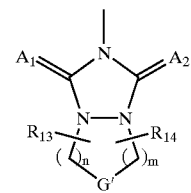

Q19 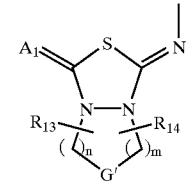

wherein $A_1$ and $A_2$ are independently oxygen or sulfur;

$R_{10}$ is hydrogen, halogen, cyano, nitro, formyl, $(C_{1-4})$alkyl, $(C_{1-4})$haloalkyl, amino, $(C_{1-4})$alkylamino, $(C_{1-4})$haloalkylamino, $(C_{1-4})$alkoxyamino, $(C_{1-4})$haloalkoxyamino, $(C_{1-4})$alkylcarbonyl, $(C_{1-4})$haloalkylcarbonyl, $(C_{1-14})$haloalkoxycarbonyl, $(C_{1-4})$alkylcabonylamino, $(C_{1-4})$haloalkylcarbonylamino, $(C_{1-4})$alkoxycarbonylamino, $(C_{1-4})$haloalkoxycarbonylamino, $(C_{1-6})$alkoxyalkyl, $(C_{1-6})$haloalkoxyalkyl, $(C_{1-6})$alkylthio, $(C_{1-6})$haloalkylthio, $(C_{2-6})$alkenyl, $(C_{2-6})$haloalkenyl, $(C_{2-6})$alkynyl or $(C_{2-6})$haloalkynyl;

$R_{11}$, $R_{12}$ and $R_{18}$ are independent of each other and may be selected from the group consisting of hydrogen, halogen, cyano, $(C_{1-4})$alkyl, $(C_{1-4})$haloalkyl, $(C_{1-4})$alkoxy, $(C_{1-4})$haloalkoxy, $(C_{2-6})$alkenyl, $(C_{2-6})$haloalkenyl, hydroxy or amino which may be optionally substituted with $(C_{1-4})$alkyl and $(C_{1-4})$haloalkyl;

$R_{13}$ and $R_{14}$ are independent of each other and may be selected from the group consisting of hydrogen, halogen, $(C_{1-3})$alkyl, $(C_{1-3})$haloalkyl, hydroxy, $(C_{1-3})$alkoxy, $(C_{1-3})$haloalkoxy, cyano, nitro, amino or $(C_{1-6})$alkylamino;

when $R_{13}$ and $R_{14}$ are taken together with the atoms to which they are attached, they represent a three to seven membered substituted or unsubstituted ring optionally containing oxygen, $S(O)_n$*** or nitrogen with following optional substitutions, one to three halogen, cyano, nitro, hydroxy, amino, carbonyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$ alkylaminocarbonyl, $(C_{1-6})$haloalkoxy, $(C_{1-6})$ haloalkoxycarbonyl, $(C_{1-6})$alkylsulfonyl, $(C_{1-6})$ haloalkylsulfonyl, aryl, heteroaryl or $(C_{3-7})$ cycloalkyl;

G is nitrogen or $CR_{16}$;

G' is $NR_{15}$, oxygen, $S(O)_n$*** or $CR_{16}R_{17}$;

G" is nitrogen, $CR_{16}$, $NR_{15}$, oxygen, $S(O)_n$*** or $CR_{16}R_{17}$;

$R_{15}$ may be selected from the group consisting of hydrogen, $(C_{1-16})$alkyl, $(C_{1-6})$alkylcarbonyl, $(C_{1-6})$ haloalkylcarbonyl, arylcarbonyl and heteroarylcarbonyl; where any of these groups may be optionally substituted with one or more of the following groups consisting of halogen, hydroxy, cyano, nitro, amino, caboxyl, $(C_{1-6})$alkyl, $(C_{1-6})$haloalkyl, $(C_{1-6})$ alkylcarbonyl, $(C_{1-6})$alkylcarbonyloxy, $(C_{1-6})$ haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$ haloalkoxycarbonyl, $(C_{1-6})$alkylsulfonyl, $(C_{1-6})$ haloalkylsulfonyl, aryl, heteroaryl and $(C_{3-7})$ cycloalkyl;

$R_{16}$ and $R_{17}$ are independent of each other and may be selected from the group consisting of hydrogen, halogen, hydroxy, mercapto, amino, cyano, $(C_{1-6})$ alkyl, $(C_{1-6})$haloalkyl, $(C_{1-6})$alkoxy, $(C_{1-6})$ haloalkoxy, $(C_{1-6})$alkoxyalkyl, $(C_{2-6})$alkynyl, $(C_{2-6})$ alkenyl, aryl, heteroaryl, aryloxy, heteroaryloxy, $(C_{3-6})$cycloalkyl, $(C_{3-6})$cyclocarbonyl, carboxy, $(C_{1-6})$ alkylcarbonyl, arylcarbonyl, $(C_{1-3})$ haloalkylcarbonyl, $(C_{1-6})$alkylcarbonyloxy, $(C_{1-6})$ haloalkylcarbonyloxy, $(C_{1-6})$alkoxycarbonyl, $(C_{1-6})$ haloalkoxycarbonyl, $(C_{1-6})$alkylthiocarbonyl, $(C_{1-6})$ haloalkylthiocarbonyl, $(C_{1-6})$alkoxythiocarbonyl, $(C_{1-6})$haloalkoxythiocarbonyl, $(C_{1-6})$alkylamino, arylsulfonylamino, arylamino, $(C_{1-3})$alkylthio, arylthio, $(C_{2-6})$alkenylthio, $(C_{2-6})$alkynylthio, $(C_{1-6})$ alkylsulfinyl, $(C_{2-6})$alkenylsulfinyl, $(C_{2-6})$ alkynylsulfinyl, $(C_{1-6})$alkylsulfonyl, $(C_{2-6})$ alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$ haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$ haloalkoxycarbonyl, $(C_{1-6})$alkylsulfonyl, $(C_{1-6})$ haloalkylsulfonyl, aryl, heteroaryl and $(C_{3-7})$ cycloalkyl;

n and m are independent of each other and represent an integer from 0 to 2; provided that m+n is 2, 3 or 4;

n** is 0 or 1;

n*** is represent an integer from 0 to 2.

2. A compound according to the claim 1 in which

X; and Y are independent of each other and are represented by halogen or cyano;

A is oxygen;

M is nitrogen;

E and L are independent of each other and may be selected from $CR_7$, $CR_8$, $CR_7R_8$, C(=O), C(=S), C(=NR_7) or $CNR_7R_8$;

$R_7$ and $R_8$ are independent of each other and may be selected from the group consisting of hydrogen, halogen, hydroxy, mercapto, amino, cyano, $(C_{1-6})$alkyl, $(C_{1-6})$haloalkyl, $(C_{1-6})$alkoxy,$(C_{1-6})$haloalkoxy, $(C_{1-6})$ alkoxyalkyl, $(C_{2-6})$alkynyl, $(C_{2-6})$alkenyl, aryl, heteroaryl, aryloxy, heteroaryloxy, $(C_{3-6})$cycloalkyl, carboxy, $(C_{1-6})$alkylcarbonyl, arylcarbonyl, $(C_{1-3})$ haloalkylcarbonyl, $(C_{1-6})$alkylcarbonyloxy, $(C_{1-6})$ haloalkylcarbonyloxy, $(C_{1-6})$alkoxycarbonyl , $(C_{1-6})$ haloalkoxycarbonyl, $(C_{1-6})$alkylthiocarbonyl, $(C_{1-6})$ haloalkylthiocarbonyl, $(C_{1-6})$alkoxythiocarbonyl, $(C_{1-6})$haloalkoxythiocarbonyl, $(C_{1-6})$alkylamino, arylsulfonylamino, arylamino, $(C_{1-3})$alkylthio, arylthio, $(C_{2-6})$atkenylthio, $(C_{2-6})$alkynylthio, $(C_{1-6})$ alkylsulfinyl, $(C_{2-6})$alkenylsulfinyl, $(C_{2-6})$ alkynylsulfinyl, $(C_{1-6})$alkylsulfonyl, $(C_{2-6})$ alkenylsulfonyl, $(C_{2-6})$alkynylsulfonyl, arylsulfonyl, where any of these groups may be non-substituted or substituted with any of the functional groups represented by one more of the following; halogen, hydroxy, cyano, nitro, amino, caboxyl, $(C_{1-6})$alkyl, $(C_{1-6})$ haloalkyl, $(C_{1-6})$alkylcarbonyl, $(C_{1-6})$ alkylcarbonyloxy, $(C_{1-6})$haloalkylcarbonyl, $(C_{1-6})$ haloalkylcarbonyloxy, $(C_{1-6})$alkoxy, $(C_{1-6})$ alkoxycarbonyl, aminocarbonyl, $(C_{1-6})$ alkylaminocarbonyl, $(C_{1-6})$haloalkoxy, $(C_{1-6})$ haloalkoxycarbonyl, $(C_{1-6})$alkylsulfonyl, $(C_{1-6})$ haloalkylsulfonyl, aryl, aryloxy, heteroaryl heteroaryloxy and $(C_{3-7})$cycloalkyl;

Q is selected from $Q_1$, $Q_2$, $Q_3$, $Q_7$, $Q_9$, $Q_{10}$, $Q_{16}$ or $Q_{17}$; wherein $A_1$ and $A_2$ are independently oxygen or sulfur;

$R_{10}$ is $(C_{1-3})$alkyl, $(C_{1-3})$haloalkyl or amino $R_{11}$ and $R_{12}$ are independent of each other and may be selected from the group consisting of hydrogen, halogen, cyano, $(C_{1-4})$alkyl, $(C_{1-4})$haloalkyl, $(C_{1-4})$ alkoxy, $(C_{1-4})$haloalkoxy, $(C_{2-6})$alkenyl, $(C_{2-6})$ haloalkenyl, hydroxy and amino, which may be optionally substituted with $(C_{1-4})$alkyl or $(C_{1-4})$ haloalkyl;

$R_{13}$ and $R_{14}$ are independently of each other and may be selected from the group consisting of hydrogen, halogen, $(C_{1-3})$alkyl, $(C_{1-3})$haloalkyl, hydroxy, $(C_{1-3})$alkoxy, $(C_{1-3})$haloalkoxy, cyano, nitro, amino and $(C_{1-6})$alkylamino;

G is nitrogen or $CR_{16}$;

G' is $NR_{15}$, oxygen, $S(O)_n$*** or $CR_{16}R_{17}$;

$R_{15}$ may be selected from the group consisting of hydrogen, $(C_{1-6})$alkyl, $(C_{1-6})$alkylcarbonyl, $(C_{1-6})$ haloalkylcarbonyl, arylcarbonyl and heteroarylcarbonyl;

$R_{16}$ and $R_{17}$ are independent of each other and may be selected from the group consisting of hydrogen, halogen, hydroxy, mercapto, amino, cyano, $(C_{1-6})$ alkyl, $(C_{1-6})$haloalkyl, $(C_{1-6})$alkoxy, $(C_{1-6})$ haloalkoxy, $(C_{1-6})$alkoxyalkyl, $(C_{2-6})$alkynyl ,$(C_{2-6})$ alkenyl, aryl, heteroaryl, aryloxy, heteroaryloxy, $(C_{3-6})$cycloalkyl, carboxy, $(C_{1-6})$alkylcarbonyl, arylcarbonyl, $(C_{1-3})$haloalkylcarbonyl, $(C_{1-6})$ alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$ alkylthiocarbonyl, $(C_{1-6})$haloalkylthiocarbonyl, $(C_{1-6})$alkoxythiocarbonyl, $(C_{1-6})$ haloalkoxythiocarbonyl, $(C_{1-6})$alkylamino, arylsulfonylamino, arylamino, $(C_{1-3})$alkylthio, arylthio, $(C_{2-6})$alkenylthio, $(C_{2-6})$alkynylthio, $(C_{1-6})$ alkylsulfinyl, $(C_{2-6})$alkenylsulfinyl, $(C_{2-6})$ alkynylsulfinyl, $(C_{1-6})$alkylsulfonyl, $(C_{2-6})$ alkenylsulfonyl, $(C_{2-6})$alkynylsulfonyl, arylsulfonyl, where any of these groups may be non-substituted or substituted with any of the functional groups represented by one more of the following; halogen, hydroxy, cyano, nitro, amino, caboxyl, $(C_1 6)$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;

n and m are independent of each other and represent an integer from 0 to 2; provided that m+n=2 or 3;

n** is 0 or 1;

n*** is represent an integer from 0 to 2.

3. A compound according to the claim 2 in which

X; and Y are independent of each other and are represented by halogen or cyano;

A is oxygen;

$R_7$, and $R_8$ are independently of each other and may be selected from the group consisting of hydrogen, halogen, hydroxy, mercapto, cyano, $(C_{1-6})$alkyl, $(C_{1-6})$haloalkyl, $(C_{1-6})$alkoxy,$(C_{1-6})$haloalkoxy, $(C_{1-6})$alkoxyalkyl, $(C_{2-6})$alkynyl ,$(C_{2-6})$alkenyl, aryloxy, heteroaryloxy, $(C_{3-6})$cycloalkyl, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl , $(C_{1-6})$haloalkoxycarbonyl, $(C_{1-6})$alkylthiocarbonyl, $(C_{1-6})$haloalkylthiocarbonyl, $(_{1-6})$alkoxythiocarbonyl, $(C_{1-6})$haloalkoxythiocarbonyl, $(C_{1-6})$alkylamino, $(C_{1-3})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be non-substituted or substituted with any of the functional groups represented by one more of the following; halogen, hydroxy, cyano, nitro, carboxy $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;

$A_1$ and $A_2$ are oxygen;

Q is $Q_1$, $Q_7$ or $Q_{17}$;

$R_{10}$ is methyl or amino;

$R_{11}$ is $(C_{13})$alkyl, $(C_{1-3})$haloalkyl, $(C_{1-3})$alkoxy or $(C_{1-3})$haloalkoxy;

$R_{12}$ is hydrogen, halogen or $(C_{1-3})$alkyl.

4. A compound according to claim 1 wherein Q is $Q_7$.

5. A process for the preparation of the compound of the formula XXV as claimed in claim 1, which comprises cyclizing a compound according to formula XXIV

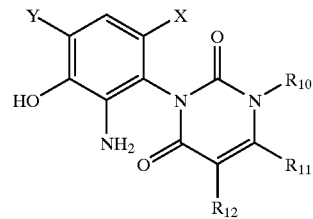

XXIV

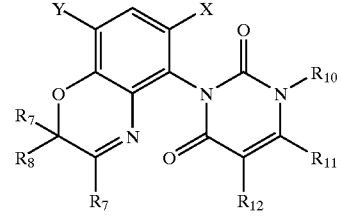

XXV wherein

X, Y, $R_7$, $R_8$, $R_{10}$, $R_{11}$ and $R_{12}$ are as previously, defined.

6. A process for the preparation of the compound of the formula XXVI as claimed in claim 1, which comprises cyclizing a compound according to formula XXIV

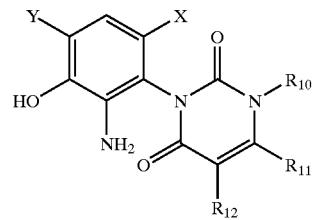

XXIV

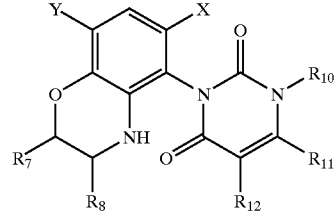

XXVI wherein

X, Y, $R_7$, $R_8$, $R_{10}$, $R_{11}$ and $R_{12}$ are as previously defined.

7. A process of the preparation of the compound of the formula XXVII as claimed in claim 1, which comprises cyclizing a compound according to formula XXIV

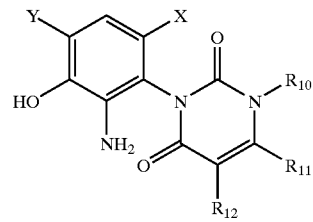

XXIV

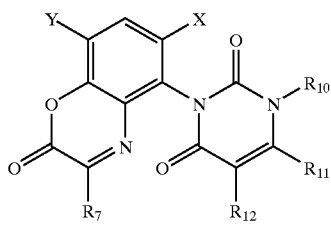

XXVII wherein

X, Y, R$_7$, R$_{10}$, R$_{11}$ and R$_{12}$ are as previously defined.

8. A process for the preparation of the compound of the formula XXVIII as claimed in claim 1, which comprises a cyclizing a compound according to formula XXIV

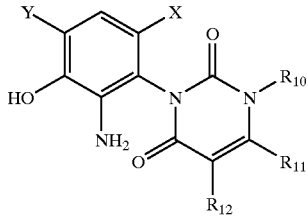

XXIV

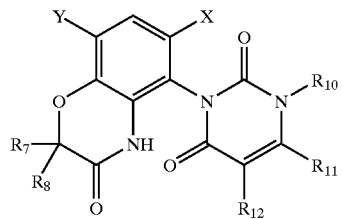

XXVIII wherein

X, Y, R$_7$, R$_8$, R$_{10}$, R$_{11}$ and R$_{12}$ are as previously defined.

9. Herbicidal composition, characterized in that it contains at least one compound according to the claim 1.

10. The herbicidal composition according to the claim 9 wherein it contains the compound of formula (Ia) or its salt and an auxiliary agent.

11. The herbicidal composition according to the claim 10 wherein it contains the compound of formula (Ia) or its salt and at least one surfactant or solid or liquid diluent.

12. A method for controlling the growth of undesired plant species in plantation crops which comprises applying to the locus of the crop a herbicidally effective amount of a compound or its salt of formula (Ia) of the claim 1.

13. A method for controlling undesired vegetation in a crop field by applying to the locus of the crop to be protected a herbicidally effective amount of a compound of the claim 1.

14. A method to defoliate potato or cotton using a compound of the claim 1.

15. A method for controlling undesired vegetation according to the claim 13 wherein the crop field is a corn or soybean field.

\* \* \* \* \*